(12) United States Patent
Eslami et al.

(10) Patent No.: US 12,070,294 B2
(45) Date of Patent: Aug. 27, 2024

(54) ENDOVASCULAR ORIFICE DETECTION DEVICE FOR ACCURATE FENESTRATED STENT GRAFT DEPLOYMENT

(71) Applicant: University of Pittsburgh—Of the Commonwealth System of Higher Education, Pittsburgh, PA (US)

(72) Inventors: Mohammad H. Eslami, Pittsburgh, PA (US); David A. Vorp, Pittsburgh, PA (US); Timothy K. Chung, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 288 days.

(21) Appl. No.: 17/603,881

(22) PCT Filed: Apr. 17, 2020

(86) PCT No.: PCT/US2020/028791
§ 371 (c)(1),
(2) Date: Oct. 14, 2021

(87) PCT Pub. No.: WO2020/214970
PCT Pub. Date: Oct. 22, 2020

(65) Prior Publication Data
US 2022/0192502 A1    Jun. 23, 2022

Related U.S. Application Data

(60) Provisional application No. 62/835,345, filed on Apr. 17, 2019.

(51) Int. Cl.
*A61B 5/00* (2006.01)
*A61B 18/00* (2006.01)
(Continued)

(52) U.S. Cl.
CPC ............ *A61B 5/0084* (2013.01); *A61B 5/489* (2013.01); *A61B 18/24* (2013.01); *A61F 2/07* (2013.01);
(Continued)

(58) Field of Classification Search
CPC ....... A61B 5/0084; A61B 5/489; A61B 18/24; A61B 2018/00345; A61F 2/07; A61F 2/954; A61F 2002/065; A61M 25/09
See application file for complete search history.

(56) References Cited

U.S. PATENT DOCUMENTS

| 5,891,133 A | 4/1999 | Murphy-Chutorian |
| 6,026,814 A | 2/2000 | LaFontaine et al. |

(Continued)

OTHER PUBLICATIONS

Supplementary European Search Report, issued in related European Patent Application No. 20792014.1, by the European Patent Office on Dec. 7, 2022, 8 pages.

(Continued)

*Primary Examiner* — Sean A Frith
(74) *Attorney, Agent, or Firm* — Klarquist Sparkman, LLP

(57) ABSTRACT

An endovascular apparatus can comprise an array of emitters configured to emit light at a predetermined wavelength and an array of sensors configured to detect light emitted by the emitters and reflected off a surface. The device can be configured to be inserted into a stent within a blood vessel of a patient and the device can be configured to detect the location of a branch blood vessel based on the reflected light detected by the array of sensors. Some devices detect light through a stent wall from an emitter positioned in the branch vessel. Some devices include fiber optics or phototransistors for receiving light from the emitter. Some devices include a fenestration former and a guidewire director along with the light receivers all in one endovascular device.

24 Claims, 19 Drawing Sheets

(51) Int. Cl.
*A61B 18/24* (2006.01)
*A61F 2/06* (2013.01)
*A61F 2/07* (2013.01)
*A61F 2/954* (2013.01)
*A61M 25/09* (2006.01)

(52) U.S. Cl.
CPC .... *A61F 2/954* (2013.01); *A61B 2018/00345* (2013.01); *A61F 2002/065* (2013.01); *A61M 25/09* (2013.01)

(56) References Cited

U.S. PATENT DOCUMENTS

| | | | |
|---|---|---|---|
| 8,473,030 B2 | 6/2013 | Greenan et al. | |
| 9,724,071 B2* | 8/2017 | Deladi | A61B 8/445 |
| 10,194,801 B2* | 2/2019 | Elhawary | A61B 5/0261 |
| 2005/0215859 A1 | 9/2005 | Chin et al. | |
| 2005/0215911 A1* | 9/2005 | Alfano | A61B 1/041 |
| | | | 600/476 |
| 2007/0208256 A1 | 9/2007 | Marilla | |
| 2008/0171934 A1 | 7/2008 | Greenan et al. | |
| 2009/0125097 A1 | 5/2009 | Bruszewski et al. | |
| 2009/0228020 A1* | 9/2009 | Wallace | A61B 34/30 |
| | | | 606/130 |
| 2010/0106175 A1* | 4/2010 | Mclachlan | A61F 2/06 |
| | | | 606/185 |
| 2012/0062714 A1 | 3/2012 | Liu et al. | |
| 2012/0209359 A1* | 8/2012 | Chen | A61B 5/411 |
| | | | 607/92 |
| 2012/0289776 A1 | 11/2012 | Keast et al. | |
| 2014/0074215 A1 | 3/2014 | Konstantino et al. | |
| 2014/0236207 A1 | 8/2014 | Makower et al. | |
| 2014/0277367 A1* | 9/2014 | Cragg | A61F 2/07 |
| | | | 623/1.12 |
| 2015/0073268 A1* | 3/2015 | Stopek | A61B 5/113 |
| | | | 600/424 |
| 2015/0209526 A1* | 7/2015 | Matsubara | A61B 17/11 |
| | | | 600/106 |
| 2015/0359630 A1 | 12/2015 | Wilson et al. | |
| 2016/0022208 A1* | 1/2016 | Gopinath | A61B 5/1076 |
| | | | 600/427 |
| 2017/0148161 A1* | 5/2017 | Griffin | A61B 5/0084 |
| 2018/0056045 A1* | 3/2018 | Donoghue | A61M 25/0068 |
| 2018/0279852 A1* | 10/2018 | Rafii-Tari | A61B 34/35 |
| 2019/0096063 A1* | 3/2019 | Ambwani | G06T 7/0014 |

OTHER PUBLICATIONS

International Search Report and Written Opinion for related International Application No. PCT/US2020/028791, 15 pages, mailed Jul. 21, 2020.

* cited by examiner

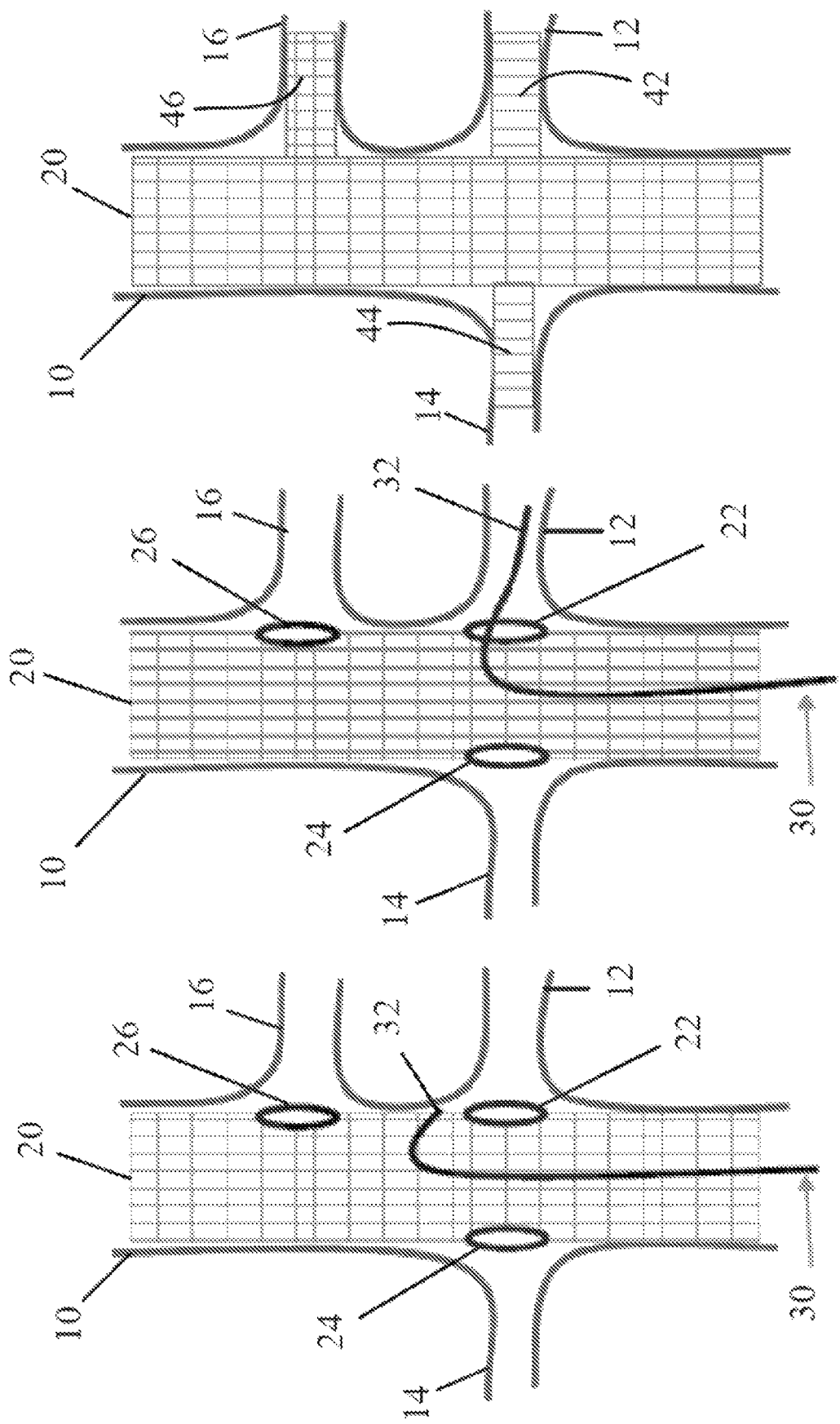

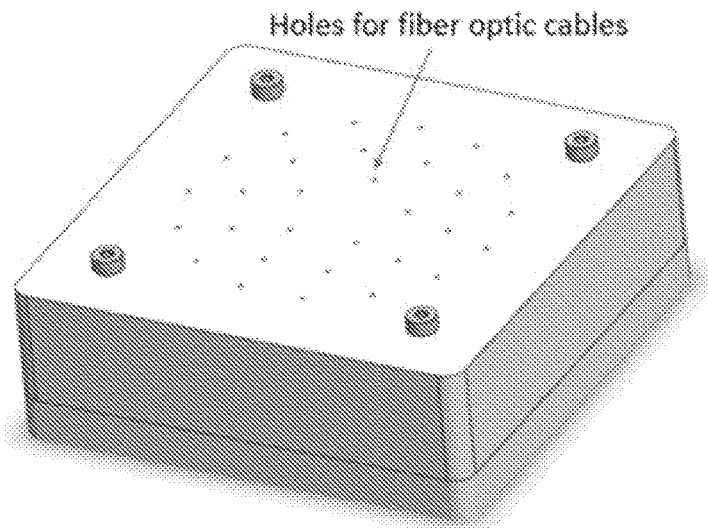
FIG. 16
FIG. 17
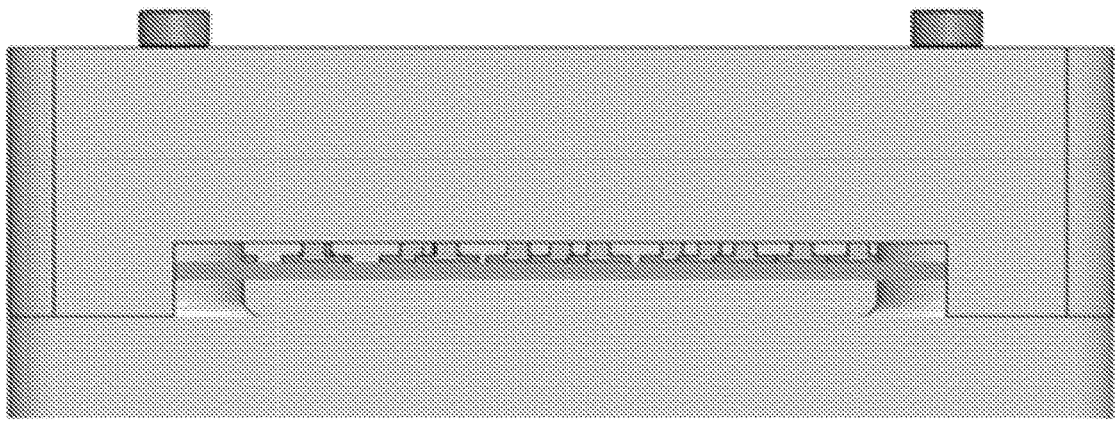
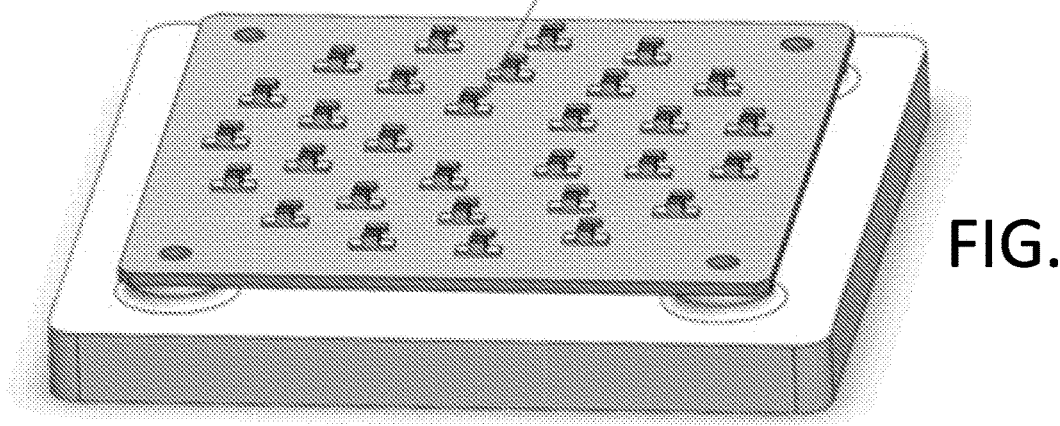
FIG. 18

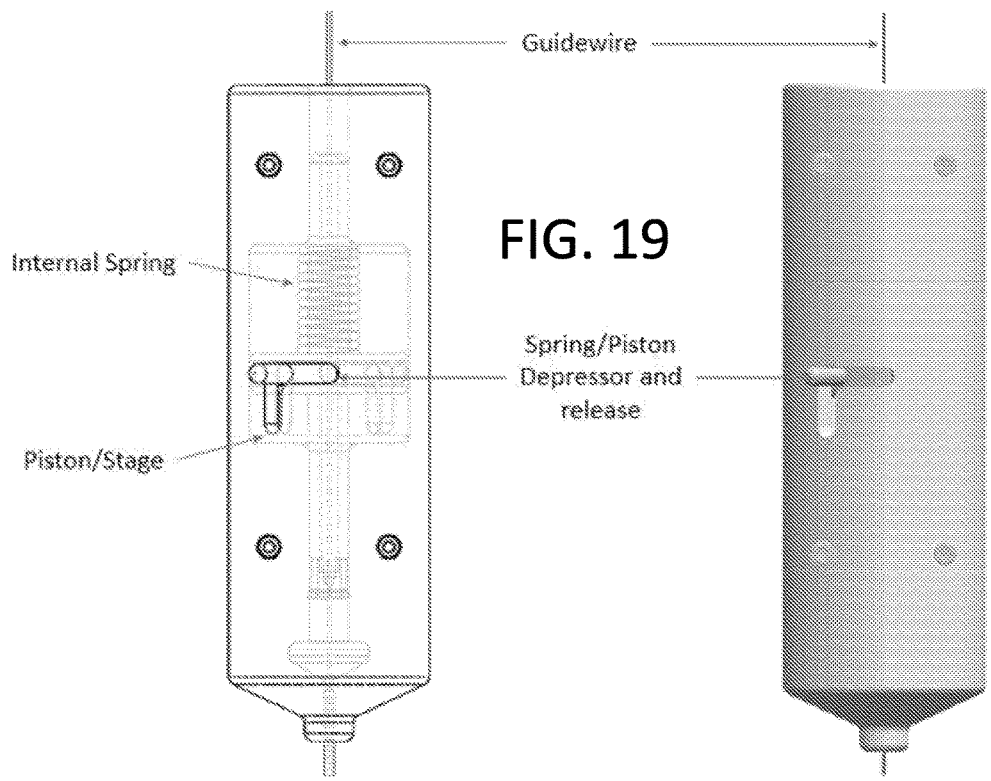
FIG. 19
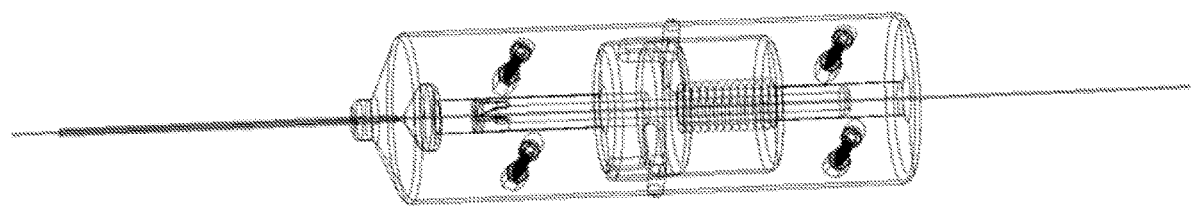
FIG. 20
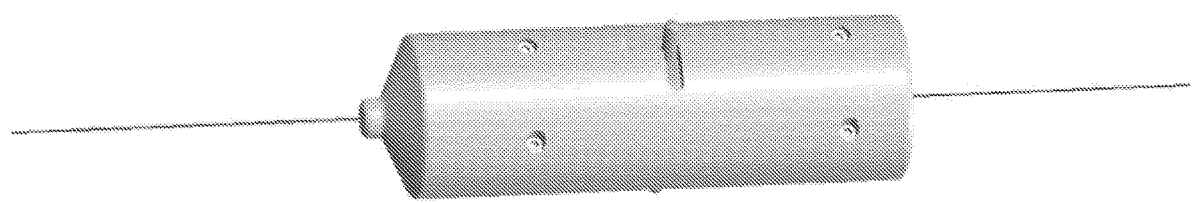

ENDOVASCULAR ORIFICE DETECTION DEVICE FOR ACCURATE FENESTRATED STENT GRAFT DEPLOYMENT

CROSS-REFERENCE TO RELATED APPLICATIONS

This application is the U.S. National Stage of International Application No. PCT/US2020/028791, filed Apr. 17, 2020, which claims priority to and the benefit of U.S. Provisional Patent Application No. 62/835,345, filed Apr. 17, 2019, which is herein incorporated by reference in its entirety.

FIELD

This application relates to medical devices, such as fenestrated endovascular stent grafts, and to methods for operating and implanting such devices.

BACKGROUND

Endovascular stent grafts are often used to repair infrarenal aortic aneurysms. Endovascular stents need a normal landing zone for success of an implantation procedure. When an aneurysmal segment extends more proximally, a more complex stent is needed. In these more complex situations, a fenestrated aortic graft may be used when the graft is positioned over orifices of arterial branches of the aorta, such as the renal, mesenteric, and/or other visceral (intestinal) arteries. Fenestrations in the stent graft provide openings for blood to flow from the aorta, through the graft, and into the arterial branches via bridging stents from the fenestrated graft to these arteries. Typically, the main tubular body of an aortic graft is implanted in the aorta first, and then each of the branches is delivered through the main tubular body, through pre-fabricated fenestrations in the tubular body of stent graft, and placed into the arterial branches extending from fenestrations radially outwardly.

Fenestrated stent grafts are specifically designed for the patient and can often take up to ten weeks to obtain due to the fabrication of patient-specific pre-fenestrations. Use of such stents are not possible during emergency cases as there is no standard pre-fenestrated stent. These stents also cannot be used in all aortic cases since there are significant anatomical constraints that must be met for a fenestrated stent graft to be appropriate. Furthermore, even with custom stent grafts, it can be very difficult and time consuming to cannulate each of the fenestrations with a guidewire in order to place the bridging stents into aortic branches. For those patients who have an urgent need for this treatment or for those patients who are not a candidate for a customized fenestrated graft, the other option is open surgery. Accordingly, there is a need in the art for devices and methods that can provide a simpler, more rapid, and safer implantation of the branches of these fenestrated endovascular graft implants. Such a device would allow for in situ fenestration in patients who present urgently with complex aortic abdominal aortic aneurysm or those who are not a candidate for custom stents.

SUMMARY

Described below are implementations of an endovascular orifice detection device for deploying fenestrated stent grafts.

In one representative embodiment, an endovascular apparatus can comprise an array of emitters configured to emit light at a predetermined wavelength and an array of sensors configured to detect light emitted by the emitters and that is reflected by or transmitted through the stent-graft material. The array of sensors can be configured to be surface mounted on the device or use fiber optics to transmit the light to an externally placed sensor array. The device can be configured to be inserted into a stent within a blood vessel of a patient. The device can be configured to detect the location of a branch blood vessel based on the reflected or transmitted light detected by the array of sensors.

In one embodiment, the array of emitters can comprise a two-dimensional array and the array of sensors can comprise a two-dimensional array. In one embodiment, the predetermined wavelength can be infrared light. In one embodiment, the apparatus can include a puncture device to puncture an outer covering of a stent graft. In one embodiment, the apparatus can include an elongated shaft with a guidewire extending through the shaft.

In another representative embodiment, a method can include inserting an orifice detection device into a stent within a blood vessel of a patient and determining the location of an orifice within the blood vessel. The orifice detection device can comprise an array of emitters to emit light and an array of sensors to detect reflected or transmitted light. The location of the orifice can be determined based on the reflected or transmitted light detected by the sensors.

In one embodiment, the method can include puncturing an outer covering of the stent at the determined location of the orifice. In one embodiment, the method can include inserting a guidewire through the orifice. In one embodiment, the method can include inserting a bridging stent through the orifice.

Some methods comprise: positioning a light emitter in a branch vessel; positioning a light detector in a main vessel, wherein the branch vessel branches off from the main vessel; detecting light from the light emitter with the light detector; and determining a location of the branch vessel based on the detected light. In such methods the light detector can comprises an array of light sensors or an array of fiber optics. Such methods can further comprise positioning a stent graft in the main vessel overlapping an orifice of the branch vessel, wherein light detector is positioned inside the stent graft and the light emitter is outside the stent graft. Once the location is determined, the method can comprise forming a fenestration in the stent graft at the determined location of the branch vessel and inserting a guidewire through the formed fenestration into the branch vessel.

Some exemplary systems disclosed herein comprise: a light emitter configured to be positioned in a branch vessel and configured to emit light from within the branch vessel; and a light detector configured to be positioned in a main vessel, wherein the branch vessel branches off from the main vessel; wherein the light detector detects the light emitted by the light emitter from within the branch vessel while the light detector is positioned in the main vessel, to determine an anatomical location of an orifice of the branch vessel. In such systems, the light detector can comprise an array of light sensors or fiber optics. In some such systems, the light emitter is coupled to a first endovascular shaft configured to extend through the main vessel and into the branch vessel, and the light detector is coupled to a second endovascular shaft configured to extend into the main vessel, and the first shaft and the second shaft independently insertable into the main vessel. The light detector can be part of a device that also includes a laser for forming a fenestration in an implanted stent graft at the determine location of the orifice of the branch vessel, and that also includes a guidewire component configured to direct a guidewire through the fenestration formed in the stent graft.

Exemplary endovascular devices disclosed herein can comprise: an optical receiver that determines a location of an orifice of a branch vessel by receiving light from a light emitter positioned in the branch vessel while the endovascular device is inside of a graft stent that is implanted in a main vessel an overlaps the orifice of the branch vessel; a fenestration former that forms a fenestration in a wall of the graft stent at the determined location of the orifice of the branch vessel; and a guidewire director that directs a guidewire through the fenestration. In some embodiments, the optical receiver comprises fiber optics, and in some embodiments, the optical receiver comprises one or more phototransistors. The fenestration former can comprise a laser component configured to direct a laser beam at the determined location of the orifice of the branch vessel, and the guidewire director can comprise a tubular guide that is oriented to direct a guidewire through the fenestration. In some embodiments, a distal end of the device can comprise a central portion that includes the optical receiver, a first lateral portion adjacent the central portion that includes the fenestration former, and a second lateral portion adjacent the central portion that includes the guidewire director. In some embodiments, the distal end of the device comprises an annular array of fiber optics that comprise the optical receiver, and an inner wall positioned radially within the annular array of fiber optics, wherein the fenestration former and the guidewire director are positioned radially within the inner wall. In some embodiments, the distal end of the device comprises an array of phototransistors that output an electrical signal in response to receiving light, and the fenestration former and the guidewire director are positioned radially within the array of phototransistors. Such phototransistors can be coupled to a printed circuit board as the distal end of the device. The distal end of the endovascular devices can flex at least 90 degrees to point toward the wall of the implanted stent graft.

The foregoing and other objects, features, and advantages of the disclosed technology will become more apparent from the following detailed description, which proceeds with reference to the accompanying figures.

BRIEF DESCRIPTION OF THE DRAWINGS

FIGS. 1A-1C illustrate a process for implanting branches of a fenestrated endovascular graft using a guidewire to cannulate each fenestration. As used herein, a fenestration includes any hole, opening, or passageway passing through a wall in a device. In FIG. 1A, a main body of the graft is implanted and a sensor probe and a guidewire are manually directed into the main body. The operator probes around until a peripheral artery is found. Immediately after the peripheral artery is found, an automatic puncturing device is deployed to create a hold in the graft material. In FIG. 1B, the guidewire is passed through a fenestration in the main body of the graft into a branch vessel. FIG. 1C shows three stented branches having been implanted using the guidewire.

FIGS. 16-18 illustrate another exemplary device similar to the device of FIG. 15, including a housing with holes for fiber optic cables.

FIGS. 19-20 illustrate an exemplary mechanical puncturing device that can be used in conjunction with the locating devices disclosed herein to create fenestrations.

DETAILED DESCRIPTION

Figure 2A:
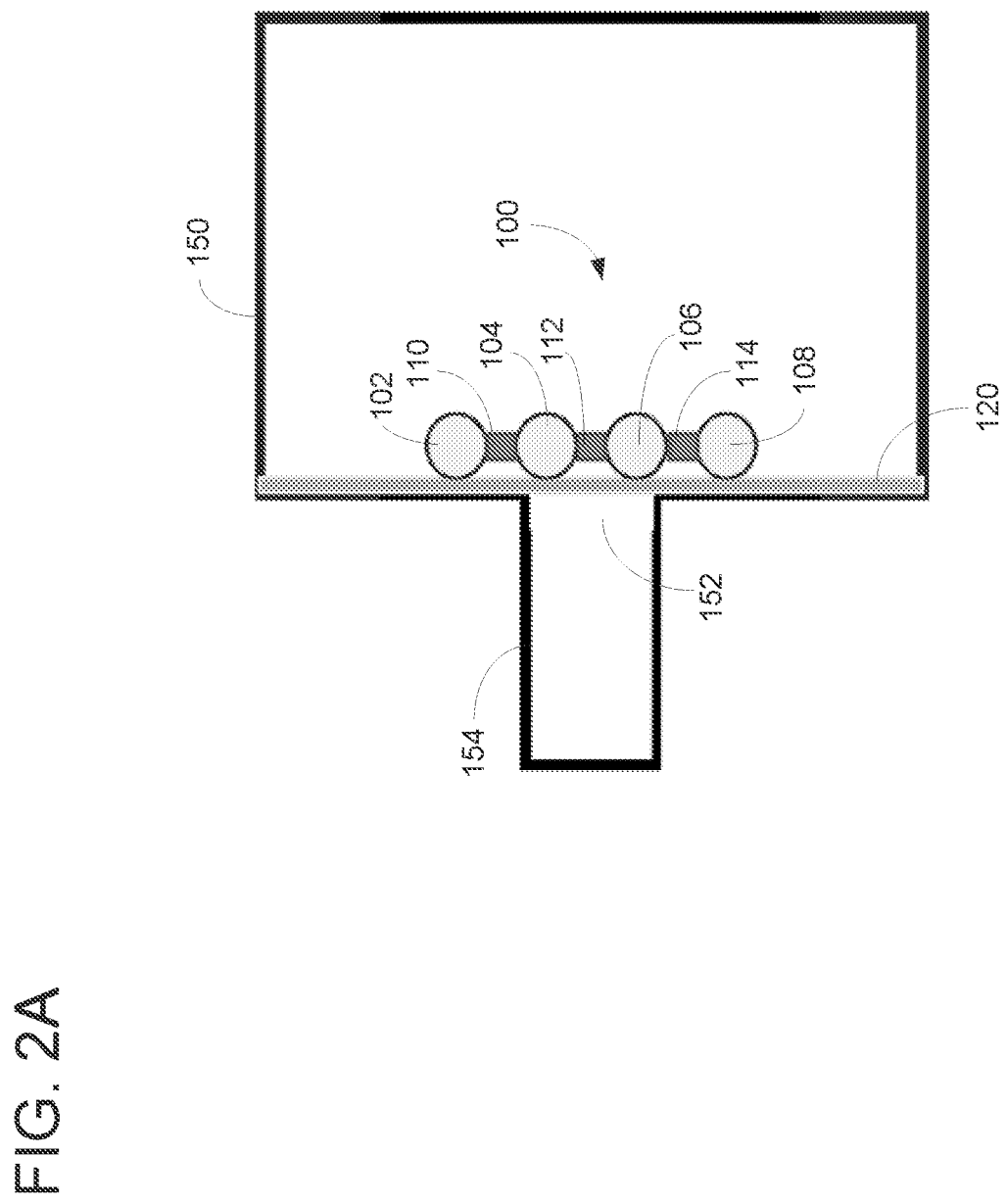
FIG. 2A shows an exemplary device for implanting a fenestrated stent graft within a patient.

Stent grafts can be used to treat weakened blood vessels and other tubular structures in the body. Stent grafts can provide rigidity and structure to maintain a vessel in an open, operative shape. Sometimes stent grafts can be used to treat aneurysms in vessels, such as aortic aneurysms (e.g., in the abdominal aorta or in the aortic arch). In other applications, stented grafts can be used to open occluded or collapsed vessels, or vessels damaged by trauma or other causes. In other applications, stented grafts can be implanted in conduit structures other than blood vessels, such as within the heart, endocrine ducts and other ducts, respiratory passages (e.g., trachea, bronchi, nasal passages), spinal canal and other nervous conduits, esophagus, intestines, urinary tract, reproductive conduits, etc. The disclosed technology is broadly applicable for use in connection to any such anatomical conduit or related application.

In some cases, a stented graft can be positioned in a section of a vessel that includes smaller vessel branches extending away from the main vessel. In such cases, a fenestrated graft can be used, including fenestrations in the graft that align with the smaller vessel branches. This allows for blood or other fluid to flow through the smaller vessel branches without unnecessary impediment from the implanted device. For example, to treat an aneurysm in the abdominal aorta, a fenestrated graft may be placed along a portion of the abdominal aorta that include the connections of the renal arteries. Such a fenestrated stent can include fenestrations that match the locations of the renal arteries so the fenestrations align with the renal arteries when implanted. Similarly, to treat an aneurysm in the aortic arch, a fenestrated graft may be placed along a portion of the aortic arch that includes the connections of the subclavian arteries, carotid arteries, and/or coronary arteries. Such a fenestrated stent can include fenestrations that match the locations of these branch arteries so the fenestrations align with the branch arteries when implanted. Other arteries that can be accommodated with this technology include the iliac arteries and superior mesenteric arteries. The disclosed technology is not limited to use in arteries, and can be used in veins, heart chambers, and in other anatomical ducts. In some methods, the locations of the fenestrations can be determined based on a CT scan or other imaging of a specific patient.

In some embodiments, a fenestrated graft can also include stent branches that extend from the fenestrations in the main tubular body of the graft a short distance outwardly from the main tubular body. These stent branches can be positioned in the smaller vessel branches when the device is fully implanted. However, the process for placing these stent branches can be very challenging and dangerous for the patient.

When implanting a stent graft within a blood vessel that has branch vessels, the stent graft must have fenestrations that match the orifices leading to these branch vessels such that blood can flow from the main blood vessel to and from the branch vessels. This typically requires the use of a prefabricated stent graft with fenestrations for the branch vessels. In order to ensure that the fenestrations in the stent graft match the orifices in the patient's blood vessel, the patient's anatomy must be imaged using x-ray or other imaging technology and the stent graft must then be fabricated appropriately. This can be an expensive and time-consuming process. Additionally, properly placing the stent can lead to other problems, as described below.

FIGS. 1A-1C illustrate an exemplary process for placing three stent branches. A section of an exemplary major vessel 10 is shown including three smaller vessel branches 12, 14, 16 extending laterally away from the major vessel 10. In FIG. 1A, the main body of an exemplary fenestrated graft 20 is shown already positioned within the major vessel 10, with fenestrations 22, 24, 26 aligned with the vessel branches 12, 14, 16. In FIG. 1A, a guidewire 30 has been introduced into the inside of the graft 20, but the tip 32 of the guidewire has missed the fenestrations and is poking into the wall of the device, which can cause damage or injury.

In order to place the stent branches (see branches 42, 44, 46 shown in FIG. 1C), the tip 32 of the guidewire 30 must first be guided through the fenestrations 22, 24, 24 (one at a time) so that vessel branches can be cannulated and the stent branches can be delivered and implanted. In some methods, the guidewire is manipulated manually while the operator looks at an imaging monitor to visualize the location of the tip of the guidewire within body. In some methods, the operator "probes around" with the tip of the guidewire until the tip is successfully placed through one of the fenestrations and into one of the vessel branches. This can be time consuming and increase exposure of the patient to risks of radiation and vascular contrast. FIG. 1B shows an example when the guidewire tip 32 has been successfully placed through the fenestration 22 into the vessel branch 12.

The process of trying to manually place a guidewire (or other device) through a fenestration in a graft and into a vessel branch can be very time-consuming, difficult, and risky. One challenge is using a 2D imaging modality such as X-ray imaging. The operator has limited vision of the true position of the guidewire tip and sometimes has to "probe around" with tip trying to get it through the desired fenestration. Not only is it difficult to guide a guidewire in a 3D space using a 2D imaging modality, but prolonged X-ray or other imaging can expose the patient to unsafe levels of radiation (e.g., cancer risk) and/or contrast use (e.g., renal failure). The medical staff may also be exposed to excessive radiation. Further, patients are kept in surgery longer and medical staff is required to spend more time when they could otherwise be treating others.

Once the guidewire 30 is successfully placed through the fenestration 22, the stent branch 42 can be delivered into the vessel branch using one or more cannulation devices that pass over the guidewire, using the guidewire to guide it into the vessel branch. This process can then be repeated to place stent branch 44 into vessel branch 14 and stent branch 46 into vessel branch 16 (as shown in FIG. 1C). In order to overcome the problems discussed above, an orifice detection device for use in implanting a fenestrated stent graft is described below.

FIG. 2A shows an exemplary endovascular orifice detection device 100. The device 100 can be used during a procedure to implant a fenestrated stent graft within a blood vessel of a patient, such as the abdominal aorta. The device 100 can detect orifices within the vessel as described below. The device 100 is shown schematically within a blood vessel 150 having an orifice 152 leading to a branch vessel 154.

Figure 2B:
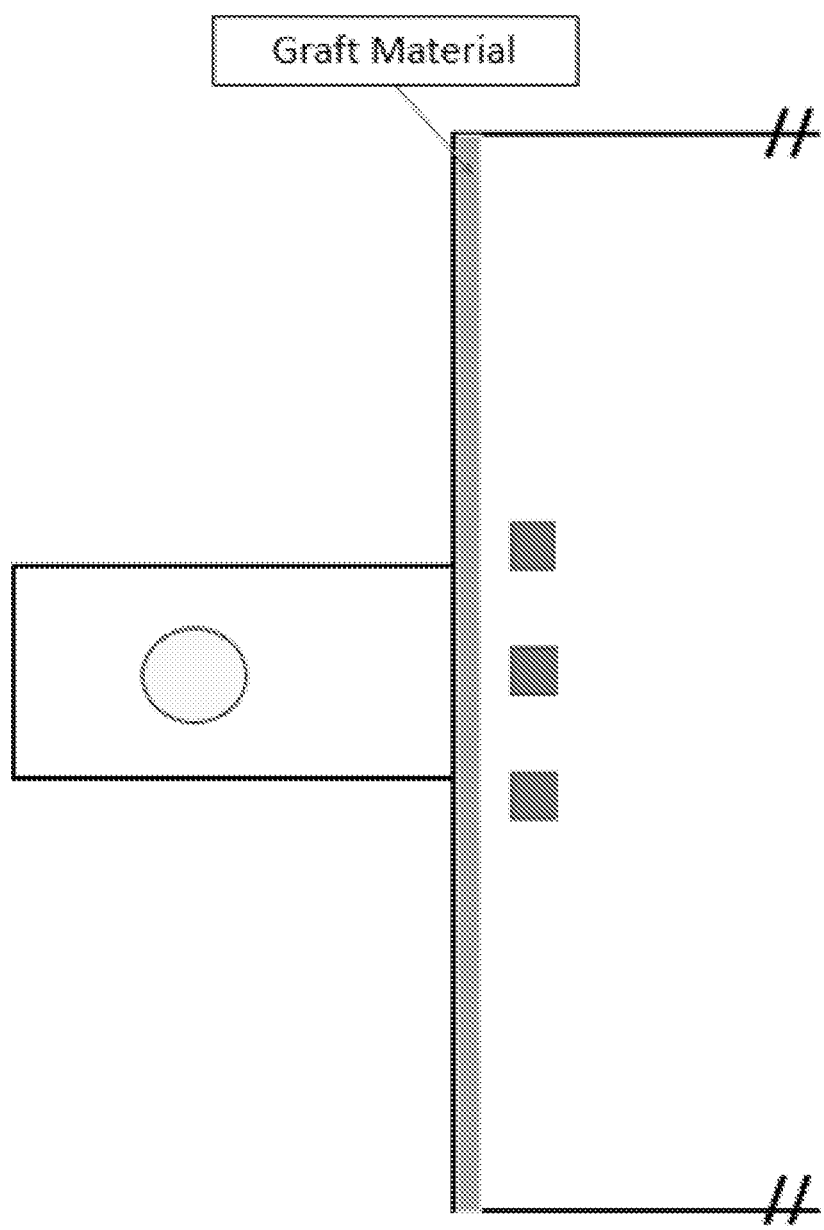
FIG. 2B illustrates an arrangement where a light source is positioned in a branch vessel while the light sensors are located inside the stent graft.

Referring to FIG. 2A, the device 100 comprises an array of sensors and light emitters. In the illustrated example, the device 100 comprises four emitters 102, 104, 106, 108 and three sensors 110, 112, 114 arranged longitudinally. In the example of FIG. 2A, the sensors 110, 112, 114 are interspersed between the emitters 102, 104, 106, 108. In other embodiments, the device 100 can have additional emitters and/or sensors. In the illustrated embodiment, the emitters 102, 104, 106, 108 emit infrared light. In other embodiments, the emitters can emit electromagnetic radiation at other wavelengths. The sensors 110, 112, 114 can detect reflections of the light emitted by the emitters 102, 104, 106, 108. Alternatively, in FIG. 2B, the emitter is placed in the visceral artery and will transmit back through the stent-graft material. The sensors will detect transmitted light from the point source.

To begin an implantation procedure using the orifice detection device 100, a stent graft without fenestrations can be implanted within the blood vessel to be treated. The stent graft can have an outer covering comprising a fabric material 120. Because the stent graft has no fenestrations, the fabric 120 initially covers the orifices to branch vessels. This can be seen in FIG. 3A, where the fabric 120 covers the orifice 152 leading to branch vessel 154. Once the stent graft has been implanted within the blood vessel, the orifice detection device 100 can be inserted within the stent graft to locate the orifices within the blood vessel. Alternatively, FIG. 3B demonstrates a point-source being placed into the visceral artery prior to stent-graft deployment. The sensor array will detect a distinct signal from the transmitted light and will begin the fenestration process.

Figure 3A:
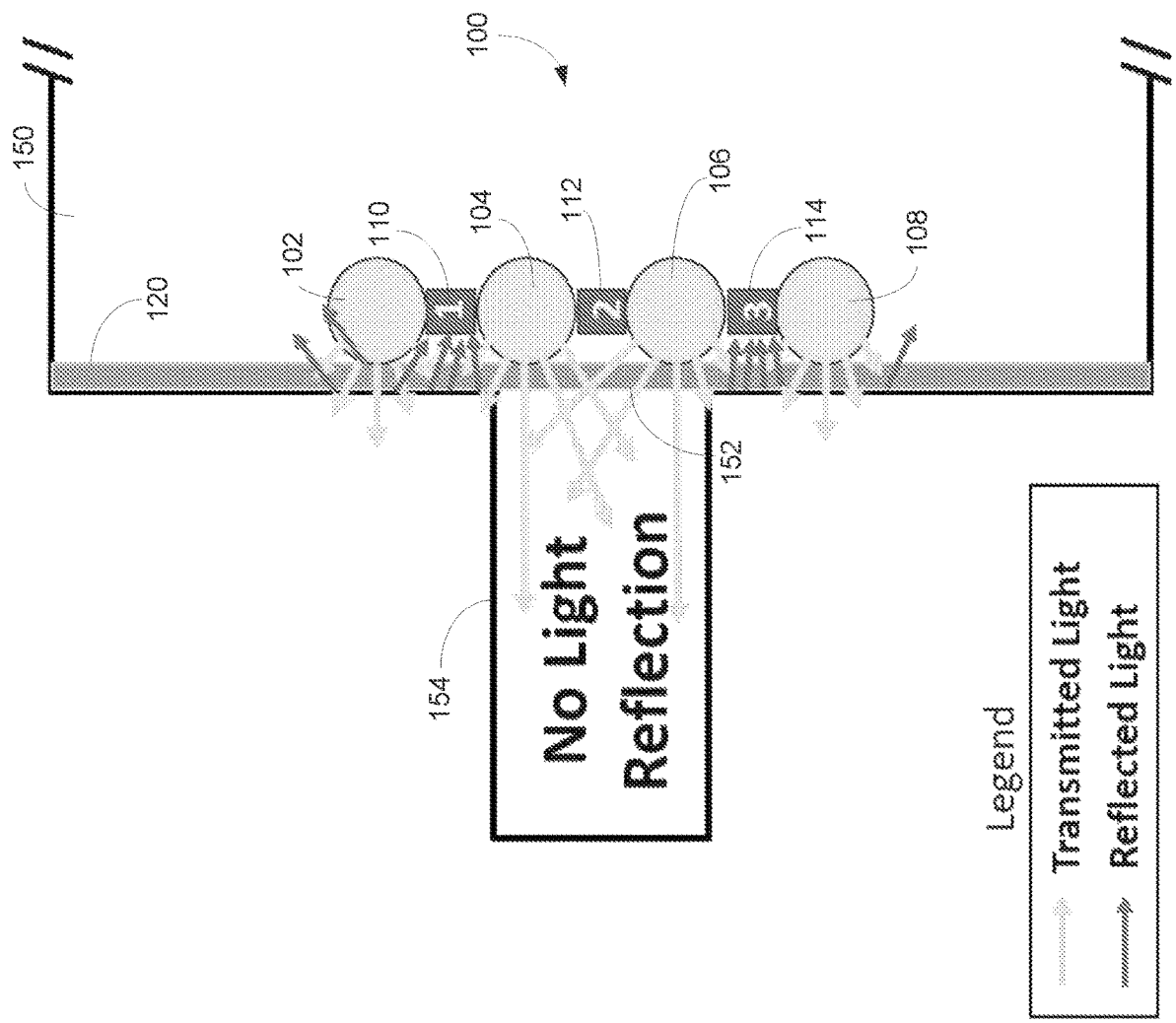
FIG. 3 shows a view of the device of FIG. 2 in operation.
FIG. 3B illustrates how light sensors inside the stent graft can detect light emitted from an emitter positioned within an adjacent branch artery.
Figure 3B:
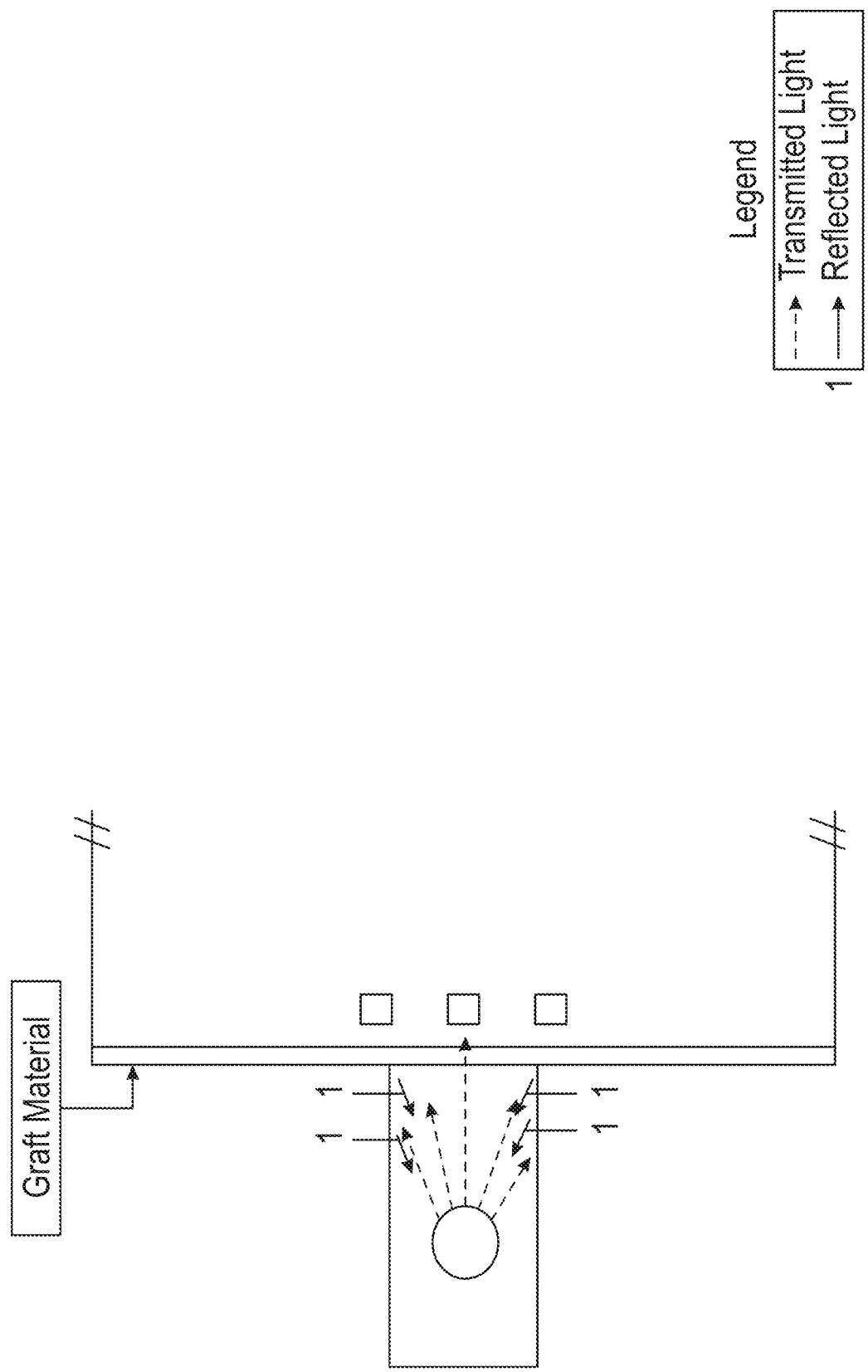

Referring to FIGS. 3A and 3B, the emitters can continually emit light, but can also be pulsed in a unique pattern to enhance detection of the signal from the sensor array. In the illustrated embodiment, the emitters emit infrared light. However, in other embodiments, the emitters can emit electromagnetic radiation at other wavelengths. The wavelength of light emitted by the emitters should be chosen such that it can transmit through the fabric 120 and reflect off of a patient's tissue.

As light is continually emitted by the emitters the light passes through the fabric 120. If the transmitted light through the fabric 120 contacts a patient's tissue, this light is reflected off of or transmitted through the tissue. However, if light passing through the fabric 120 instead encounters an orifice to a branch vessel, the light is either not reflected or weakly reflected back. The sensors 110, 112, 114 can then detect the reflected signal and based on the strength of the reflected or transmitted signal, determine whether an orifice is present at a particular location. Referring to FIG. 3A, emitted light will be detected by the sensors 110 and 114 because those sensors are adjacent a patient's tissue. However, emitted light will not be reflected back to sensor 112 because that sensor is adjacent orifice 152. Therefore, based on this reflection pattern it can be determined that there is an orifice adjacent sensor 112. In embodiments that have additional sensors and emitters, a higher resolution can be achieved. The device 100 can be moved around the inner surface of the stent to find the locations of all orifices leading to branch vessels. In FIG. 3B, transmitted light can be detected by the sensors based on the strength of the transmitted light.

Figure 4:
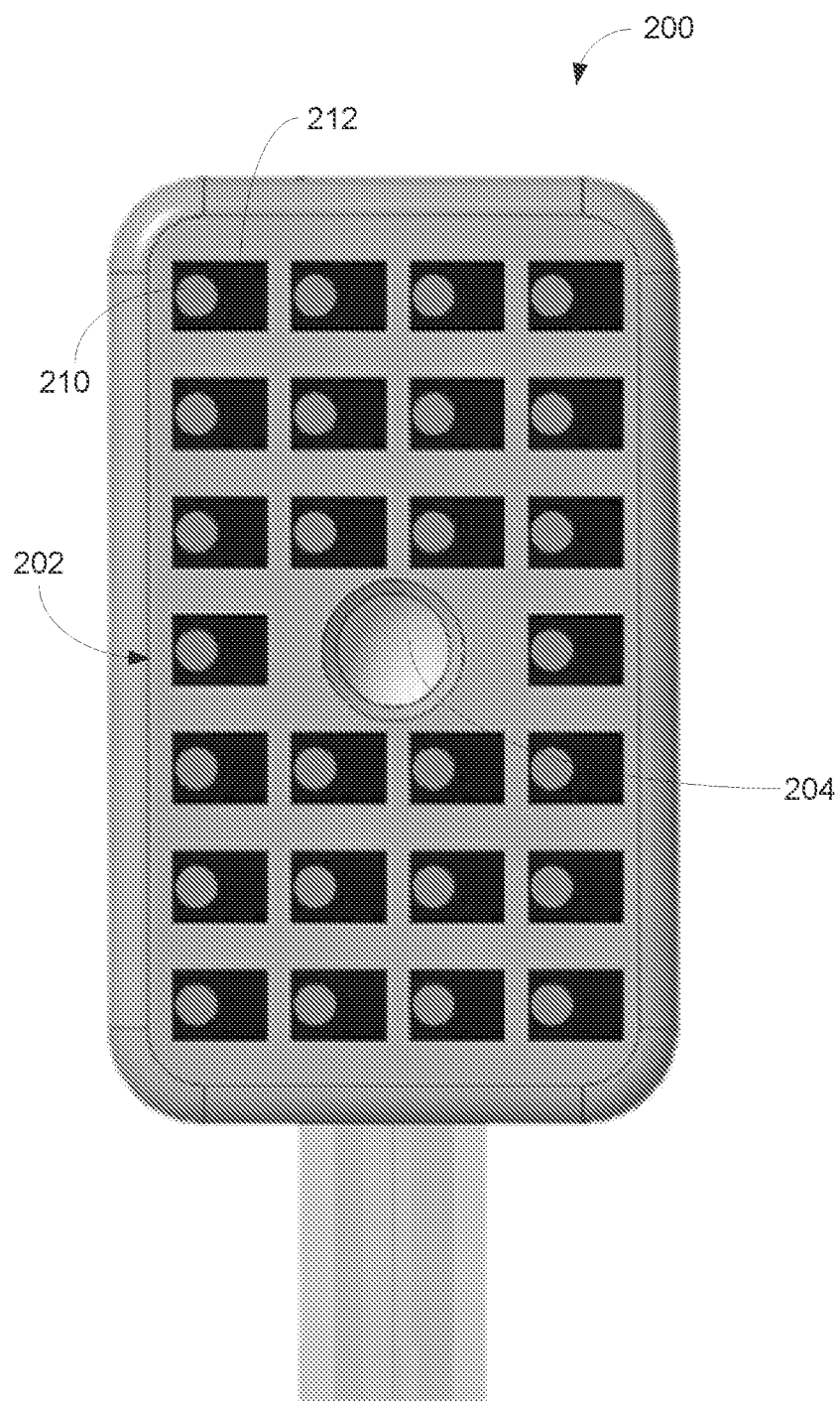
FIGS. 4-5 show front views of another exemplary device for implanting a fenestrated stent graft within a patient.

FIG. 4 shows an exemplary orifice detection device 200. In the illustrated example of FIG. 4, the device 200 contains a two-dimensional array 202 of sensors and emitters. Each element of the array 202 comprises a sensor and an emitter such as emitter 210 and sensor 212 shown in FIG. 4. The emitters can emit infrared light (or in some examples, light at other wavelengths as described above), and the sensors can detect reflected or transmitted light emitted by the emitters. In the example of FIG. 4, the array 202 contains seven rows and four columns of sensor/emitter elements. In other examples, the array 202 can contain additional sensor/emitter elements.

The operation of the device 200 can detect orifices in a blood vessel in a similar manner as described above in connection with device 100. That is, the device 200 can be moved around the inner surface of a stent graft within a patient's blood vessel while the emitters of the array 202 are continually emitting infrared light. The sensor associated with each emitter can detect the strength of the reflection of the emitted light. For each sensor/emitter element adjacent to tissue, a strong reflection will be detected and for each sensor/emitter element adjacent an orifice, a weak reflection or no reflection will be detected. Accordingly, the orifice detection device 200 can determine the locations of the orifices within a patient's blood vessel. Because the device 200 has a two-dimensional array of sensors/emitters, a more accurate mapping of the orifice locations can be determined than the device 100, which only has a one-dimensional array of sensors/emitters.

Figure 5:
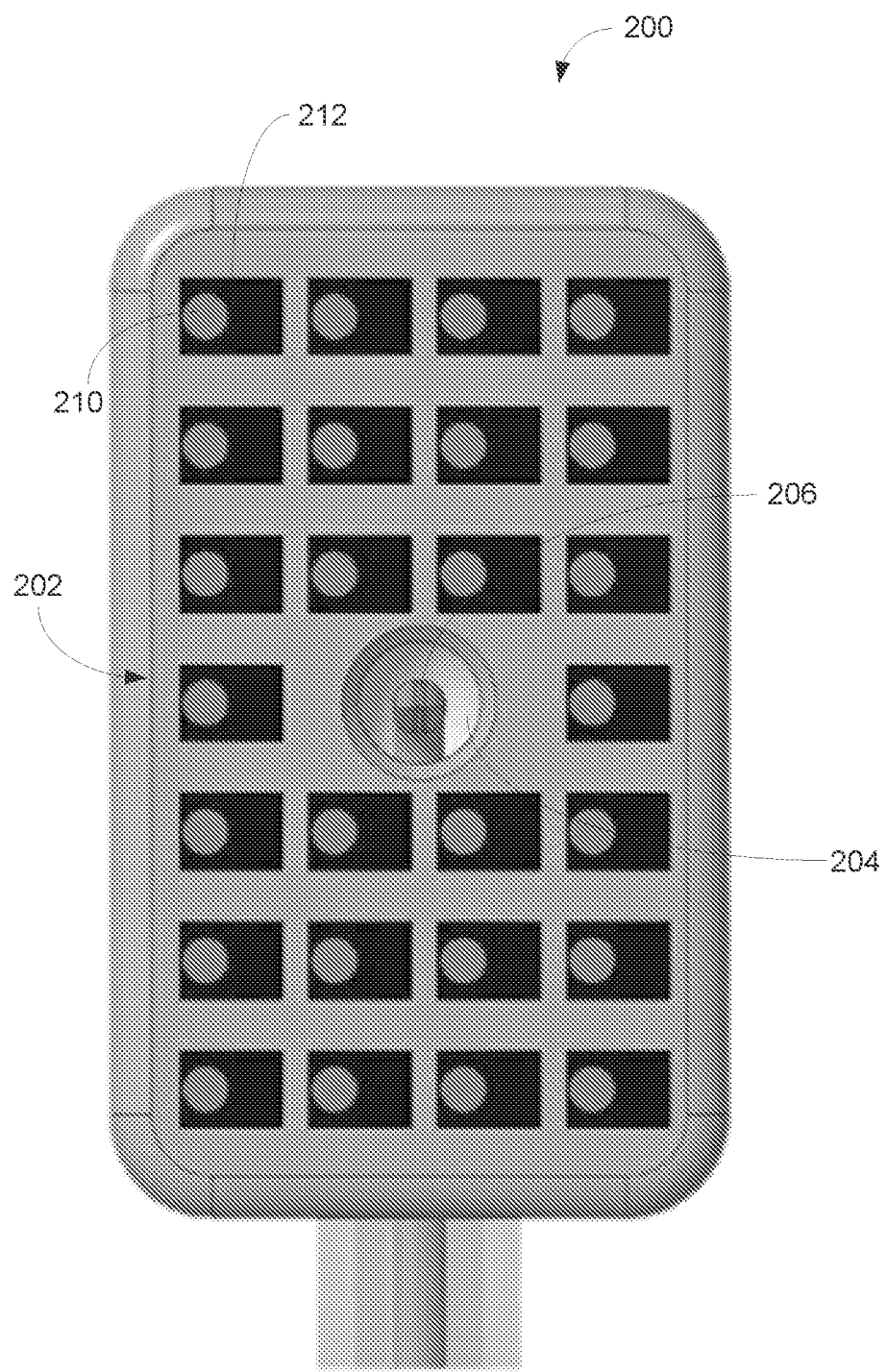
Figure 6:
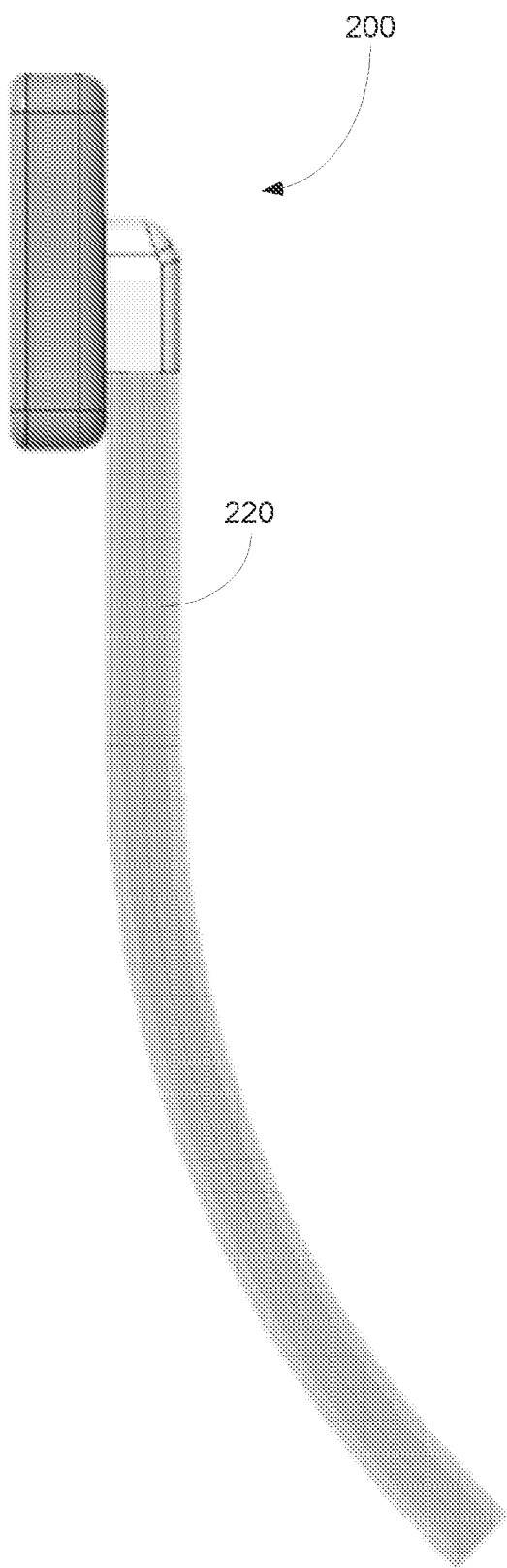
FIGS. 6-7 show side views of the device of FIGS. 4-5.

In addition to finding the location of orifices within a blood vessel, the device 200 can also be used to create fenestrations in a stent graft. Referring to FIG. 5, the device 200 can have an opening 204 at its center and a puncture device 206 that can extend through the opening 204. The puncture device 206 can comprise a needle or other mechanism that can puncture the fabric covering of a stent graft. After an orifice is found using the technique described above, as shown in FIG. 6, the puncture device 206 can extend through the opening 204 and puncture the fabric 120 of a stent graft, as shown in FIG. 7.

Figure 7:
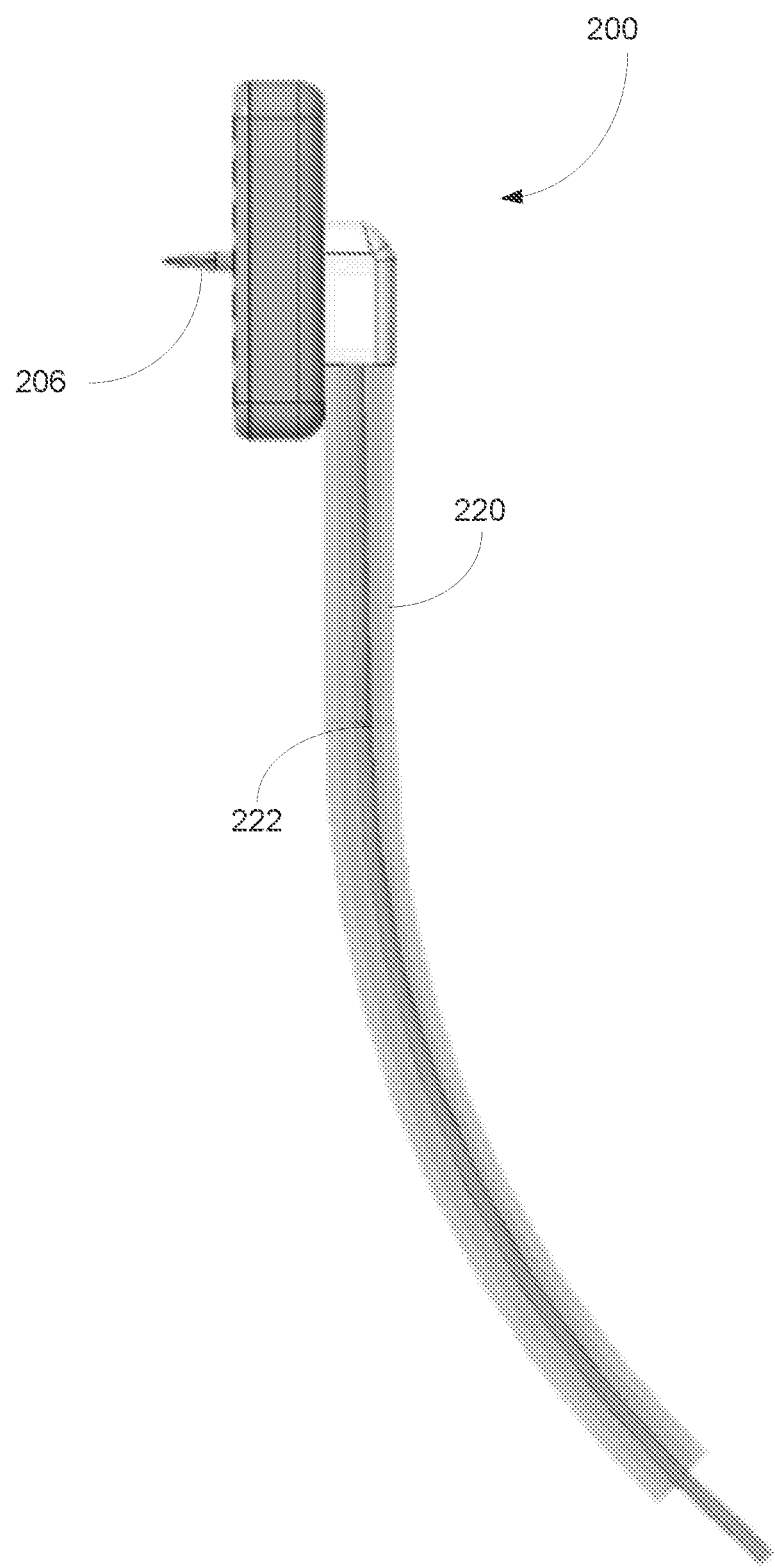
Figure 8:
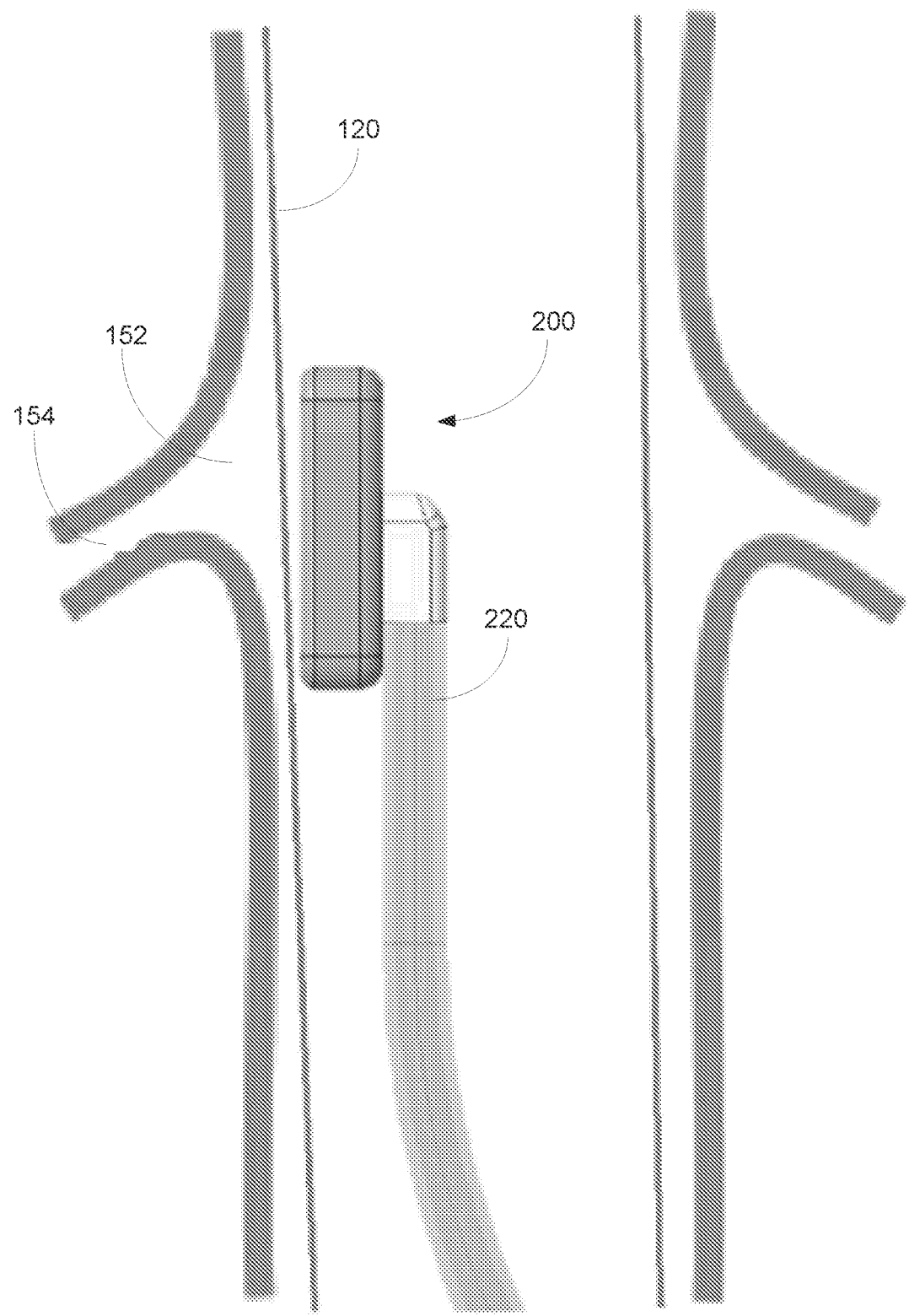
FIGS. 8-10 show the device of FIG. 4-5 within a blood vessel.
Figure 9:
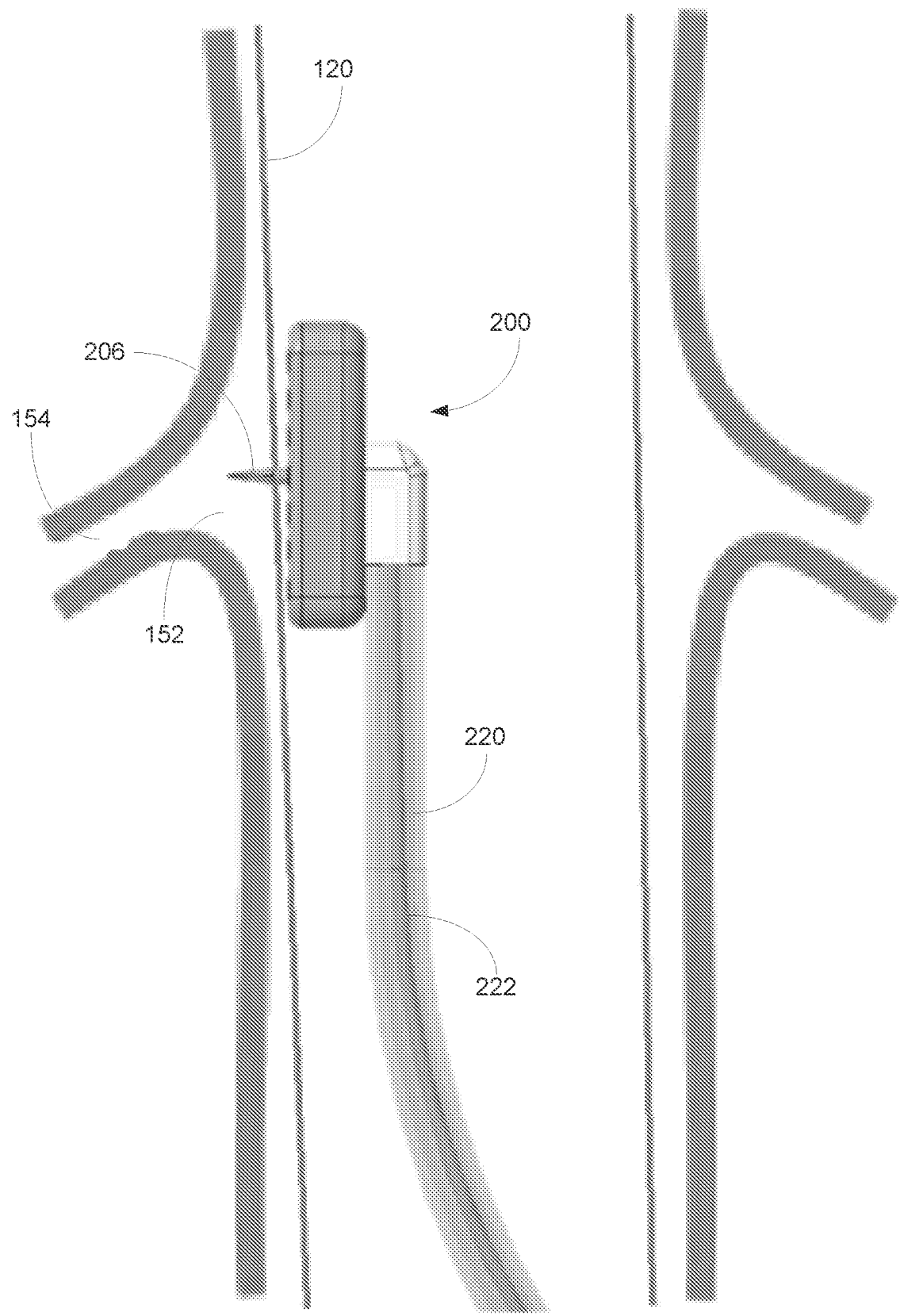
Figure 10:
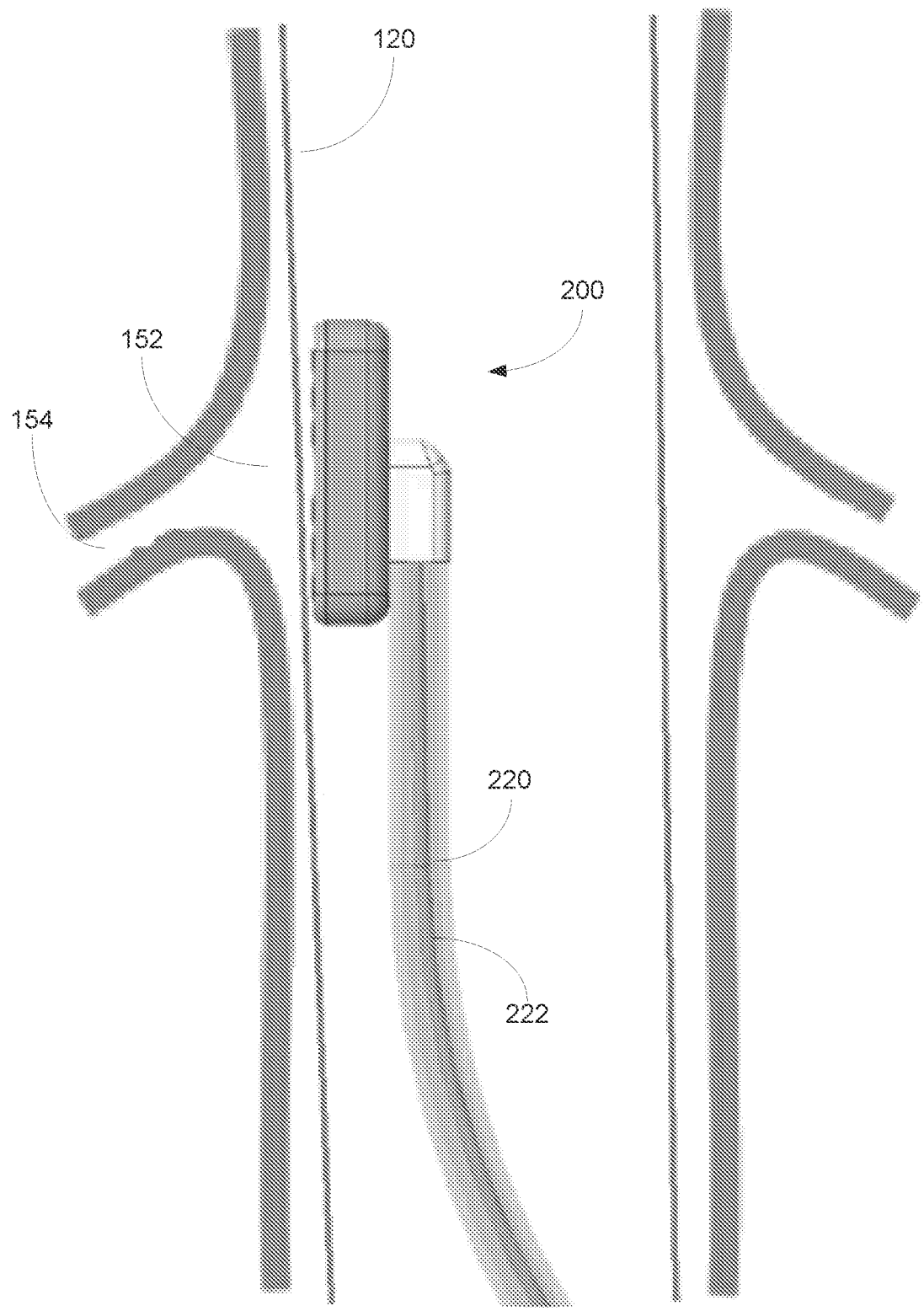

In the illustrated example, the orifice detection device 200 can be connected to a shaft 220, as shown in FIGS. 6-10. A guidewire 222 can extend through the shaft 220, as shown in FIGS. 7 and 9-10. After the puncture device 206 punctures the fabric 120 at the appropriate location, the guidewire 222 can be advanced through the shaft 220 through the orifice 152 into the branch vessel 154. A bridging stent can then be implanted in the branch vessel 154 using the guidewire 222. The orifice detection device 200 can then continue to be moved through the blood vessel to find all the orifices leading to branch vessels so that bridging stents can be implanted in all of them. The device 200 can then be removed from the patient.

Figure 11:
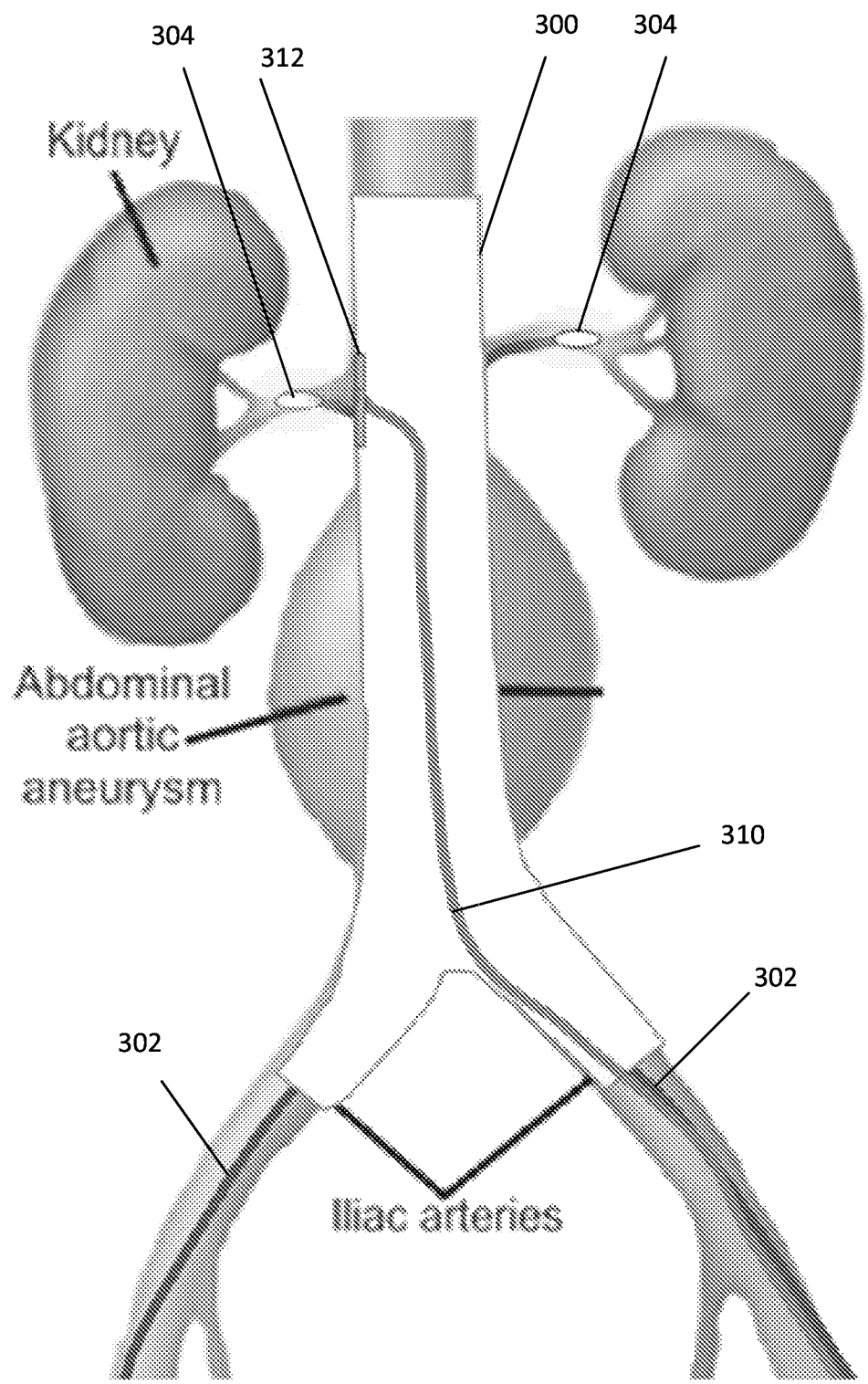
FIG. 11 shows an exemplary device for locating and forming fenestrations in a stent graft within a patient.

FIG. 11 shows an exemplary system for detecting the locations of branch arteries and creating fenestrations in the wall of a stent graft. A stent graft 300 is shown implanted in the abdominal aorta with lower branches in the iliac arteries, for treating an abdominal aortic aneurysm. Fenestrations need to be formed for the renal arteries.

In this example, light emitters 304 have been inserted into the renal arteries at the ends of shafts 302. The emitters 304 can be placed prior to placement of the stent graft 300, and the shafts 302 can be positioned between the outside of the stent graft 300 and the inside of the vessels. The emitters 304 can be configured to produce light or other electromagnetic waves. The emitted light can comprise visible light, IR light, UV light, and/or other wavelengths. In some embodiments, longer wavelengths (e.g., IR) can be desired, such as for traveling further distances and/or through blood, graft walls, or other media. The shafts 302 can comprise fiber optics to transmit light to the emitters, or the shafts can comprise wires to transmit electrical signals to the emitters, causing the emitters to create the light locally.

With the emitters 304 and the stent graft 300 in place, the detection device 312 can be introduced via shaft 310 into the stent graft to a location adjacent a renal artery. The device 312 can comprise one or more light sensors that can detect the light emitted from the emitter 304 and determine where to form a fenestration in the wall of the stent graft. The user can move the device 312 around until it is determined that it is positioned directly over the renal artery orifice. In some embodiments, the device 312 can include a 2D array of multiple light sensors, like in the device 200, for example. For example, the detection device can comprise a 3-by-3 array of sensors, or any other arrangement of sensors disclosed herein. The sensors can be electrically or optically coupled to a control device outside the body to process the detected signals. In some embodiments, the sensors are coupled to a printed circuit board, such as a collapsible printed circuit board that has a very small collapsed profile that allows it to pass through the vasculature easier.

The device 312 can further include a laser or other puncturing device to create a hole/fenestration in the wall of the stent graft as the location of the renal artery, based on the detected light from the emitter. This process can then be repeated for the other renal artery using the light from the other emitter 304. This system and method can also be used to form fenestrations for other branch arteries as well.

An image can be generated by the light detector of the device based on the light received from the emitter 304 through the wall of the stent graft. Such an image can be generated by an external device electrically or optically coupled to the device 312. In such an image, certain colors can represent higher intensity light reception, whereas other colors can represent lower intensity light reception. Crossed lines in the image can represent the location of where the fenestration is to be formed. The device 312 can be moved around by the user until the crossed lines align with the color zone of higher light intensity, indicating that the emitter is directly in front of the detector, and then the fenestration can be formed (e.g., by laser or other mechanism) in that location such that it is aligned with the renal artery orifice.

Figure 12:
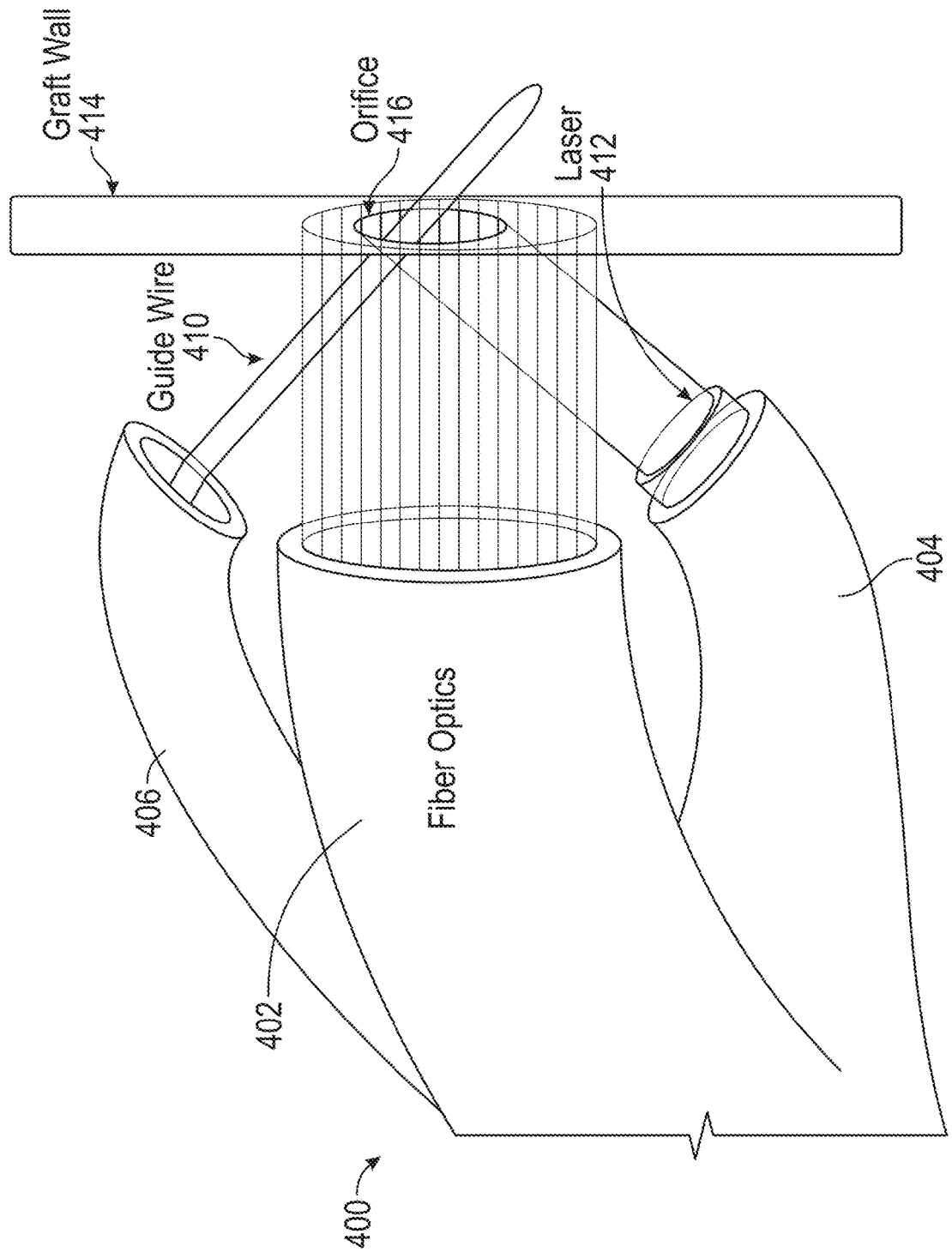
FIG. 12 shows another exemplary device for locating and forming fenestrations in a stent graft within a patient, using fiber optics to receive light.

FIG. 12 shows another exemplary device 400 for locating and forming fenestrations. The device 400 comprises an endovascular device that includes three branches at the distal end, a central branch 402 comprising a bundle of fiber optics, a first lateral branch 404 comprising a laser 412, and a second lateral branch 406 comprising a guidewire 410. The fiber optics branch 402 can comprise any number if individual fibers, such as at least 100 fibers, where a larger number of fibers can provide a higher resolution map of the light from the emitter (see FIG. 12). As shown in FIG. 12, the fiber optics branch 402 can detect the location of the renal artery (or other branch artery) by sensing light from an emitter that is pre-positioned in the branch artery (like is the system of FIG. 11), then the laser 412 can create an orifice 416 in the graft wall 414 at the determined location, and then the guide wire 410 can be directed through the orifice 416. The guidewire 410 can then be used to place a branch stent extending from the orifice 416 in the graft wall.

Furthermore, the fiber optics can sense the distance from the end of the fiber optics to the emitter based on the intensity of the sensed light, with more intense light indicating the emitter is closer and less intense light indicating the emitter is farther from the fiber optics. This can enable the operator to adjust the distance between the device 400 and the graft wall 414 accordingly.

The laser 412 can quickly cut/burn an orifice, such as the orifice 416, in the graft wall using a sufficiently high energy source such that the duration of the laser application is short and minimizes any damage to surrounding vessel walls or other structures.

The all-in-one nature of the device 400 can save time, as the device can locate the emitter positioned in the visceral artery, form the orifice by creating a fenestration through the stent graft material, and introduce the guidewire through the orifice all in quick succession using the same device without having the move the device from its location shown in FIG. 12. The angles of the lateral branches 404 and 406 can be predefined such that they are automatically aligned when the distal end of the fiber optics branch 402 is at the certain distance from the graft wall, as shown in FIG. 12.

Figure 13:
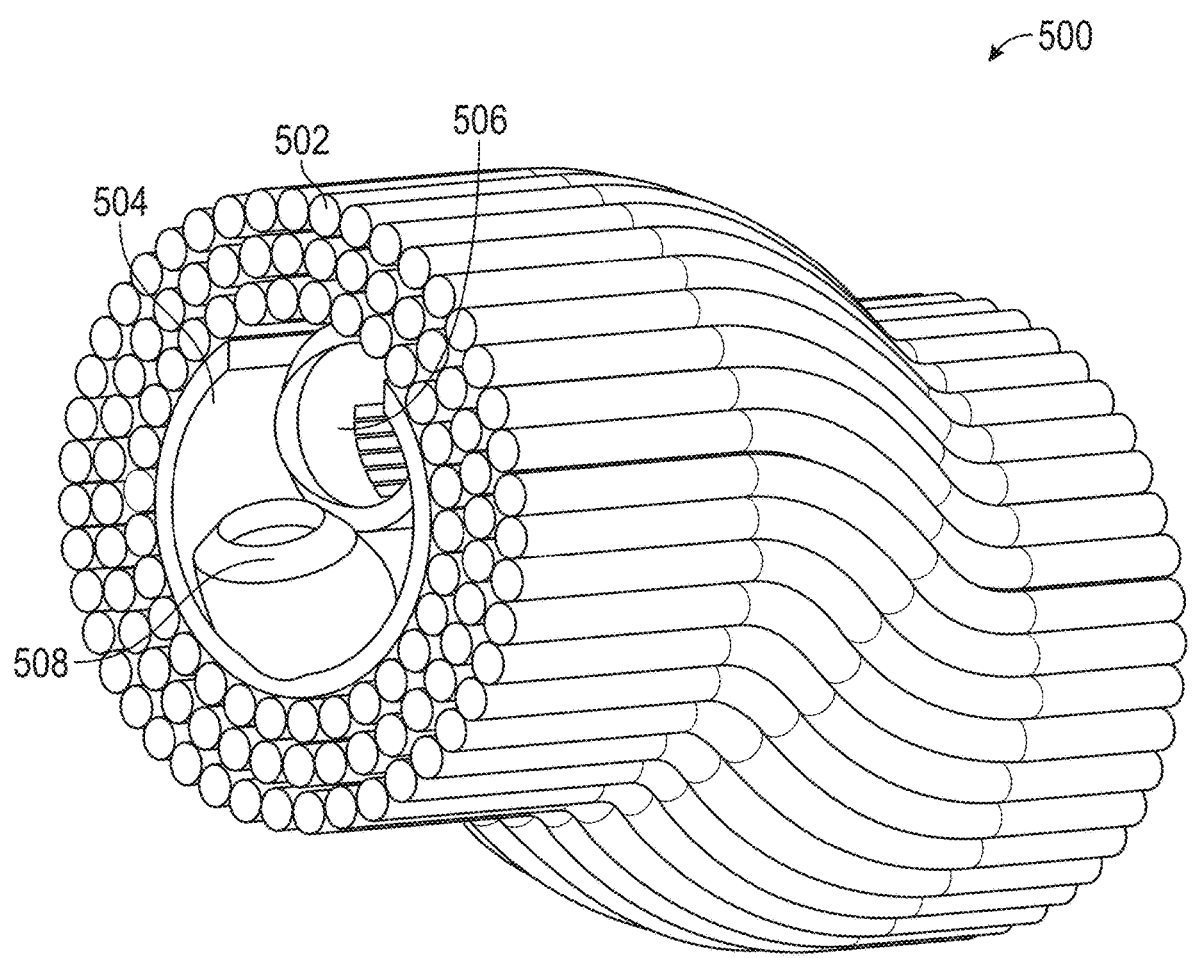
FIG. 13 shows another exemplary device for locating and forming fenestrations in a stent graft within a patient using fiber optics to receive light.

FIG. 13 shows another exemplary device 500 for locating and forming fenestrations. The device 500 comprises an endovascular device that includes an outer annular group fiber optics 502, an inner wall 504 located radially inside of the fiber optics, a laser emitter 506 positioned within the inner wall 504, and a guidewire director 508 also positioned with the inner wall. The fiber optics group 502 can comprise any number of individual fibers, such as at least 10 or at least 100 fibers, arrayed around the inner wall. The inner diameter of the fiber optics group can be such that the fiber optics can still detect when the light source is aligned with the center of the device, such as less than 3.5 mm in one example. The external diameter of the fiber optics can be small enough to allow the device to pass easily through the vasculature, such as 5.5 mm or less. An outer diameter of 5.5 mm is well under an 8 mm maximum size for enabling safe passage through an endovascular catheter.

The inner wall 504, laser emitter 506, and guidewire director 508 can be formed in any suitable manner, such as injection molding, casting, or 3D printing for example, and from any suitable materials. Parts of the laser emitter 506 and/or the guidewire director 508 can be co-formed with the inner wall and/or attached to the inner wall (e.g., adhesively, welded, etc.).

Similar to the device 300, the fiber optics group 502 can detect the location of the renal artery (or other branch artery) by sensing light from an emitter that is pre-positioned in the branch artery, then the laser 506 can create an orifice in the graft wall at the determined location, and then the guide wire director 508 can guide a guidewire through the orifice. The guidewire can then be used to place a branch stent extending from the orifice in the graft wall.

The device 500 comprises a single cohesive distal face, with the laser and guidewire components contained within the fiber optics, making the device easy to place and operate, and avoiding external projections that can get caught on stent or vessel walls. The fibers on the outside of the device can be bound together (e.g., using an adhesive or welding) and form smooth circular or other rounded outer profile. An outer sheath can be positioned around the fiber optics in some embodiments, and/or containment rings can be positioned around the fiber optics and intervals along the axial length of the device. The arrangement of the fiber optics can allow the distal end of the device to bend up to 90 degrees without losing integrity. Multiple bends can be imparted in the device, as shown in FIG. 13, to navigate the vessels and orient the distal end facing the graft wall.

Figure 14:
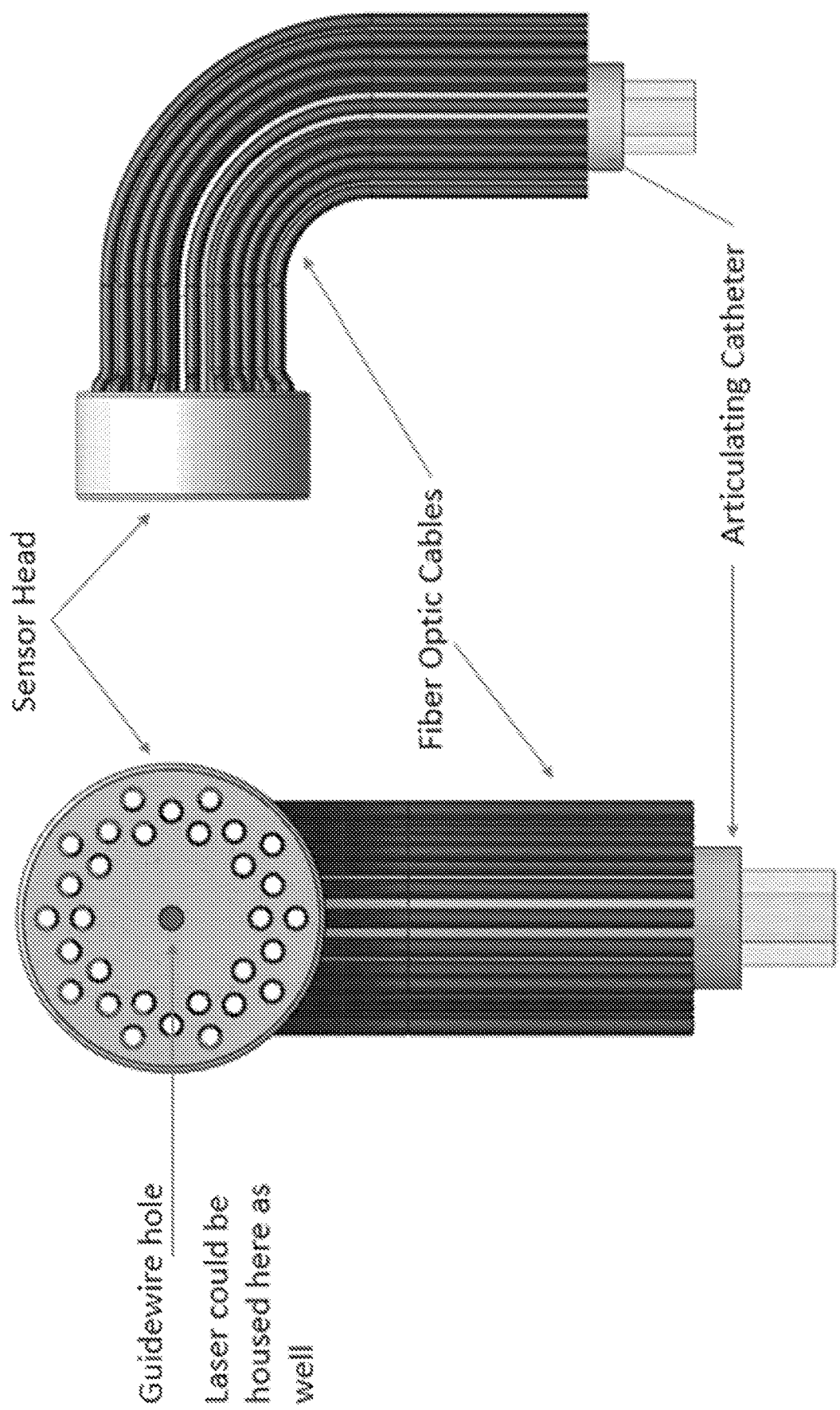
FIG. 14 shows another exemplary device similar to the device of FIG. 13.

FIG. 14 illustrates another exemplary device similar to the device 500, comprising external fiber optic cables mounted around an articulating catheter and guided through openings in a distal sensor head. The sensor head can include a central hole for the guidewire to pass through, and in some embodiments a laser-based or mechanical fenestration creation device can be positioned within the catheter with a distal portion integrated with the sensor head.

Figure 15:
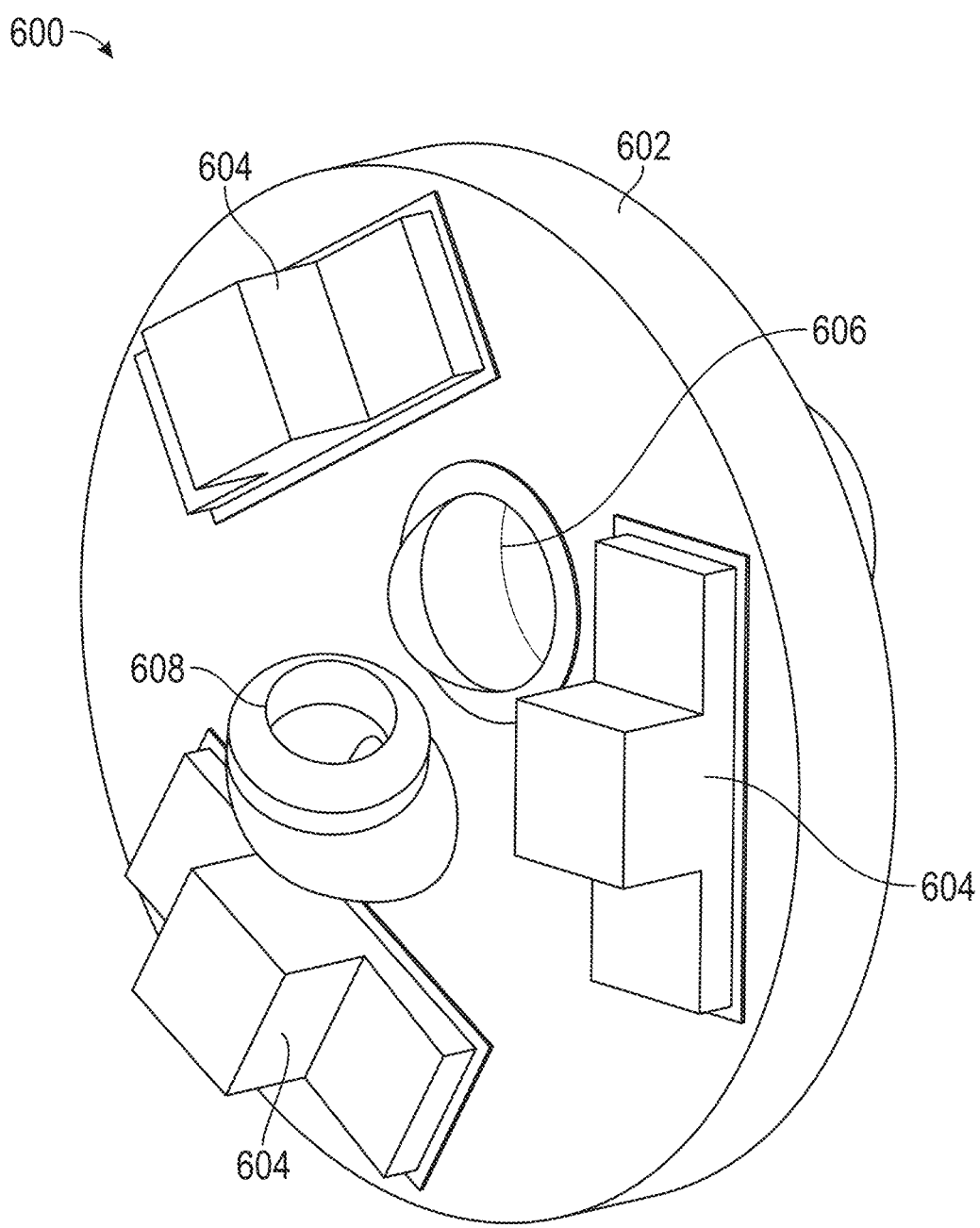
FIG. 15 shows yet another exemplary device for locating and forming fenestrations in a stent graft within a patient, using phototransistors to detect light.

FIG. 15 shows another exemplary device 600 that is configured to be positioned at the distal end of a catheter or other endovascular device for locating and forming fenestrations and deploying a guidewire through the fenestration. The device 600 comprises a base 602 (e.g., a printed circuit board or other structure) 602 that is placed inside a stent graft near the location of a desired fenestration, opposite from a pre-placed emitter. The device includes photo sensors 604 arrayed around the base (e.g., 3 or more sensors) that are capable of detecting light from the emitter. The photo sensors 604 can be very small, such as 1.25 mm×3.3 mm in one embodiment. The photo sensors 604 can comprise phototransistors, for example. The sensors 604 can output electrical signals corresponding to the sensed light, and the electrical signals can be transmitted from the device 600, through a catheter via wires, and to an external controller. This avoids the need for fiber optics running the whole length of the catheter to an external light sensor. Each of the photo sensors 604 can be coupled to a single fiber optic cable, which can be coupled to a local processor on board the device 600, or can be coupled to an external processor.

The base can be rigid or flexible/foldable. In some embodiments, the base can have a diameter of 8 mm or less, or 6 mm or less. The device further comprises a laser emitter 606 and a guidewire director 608 coupled to the base 602. The laser emitter 606 and the guidewire director 608 can be positioned within the outer array of sensors, similar to the arrangement of the device 500. The components 606, 608 can comprise separately formed parts and/or parts that are embedded or integrated in the base 602. The base can be coupled to the distal end of a catheter or other flexible/directable endovascular device.

FIGS. 16-18 illustrate another exemplary embodiment similar to the device 600, comprising a distal body for detecting light that can be coupled to the distal end of a catheter. The distal body can include a housing with a printed circuit board (or similar structure) having an array of photosensors thereon positioned within the housing. The housing can include holes in one side for fiber optic cables to pass through and couple to the photosensors of the printed circuit board.

FIGS. 19-20 illustrate an exemplary mechanical puncturing device that can be used in conjunction with any of the herein disclosed sensing/locating devices to create fenestrations in a stent wall. The mechanical puncturing device can include an outer housing with a passage therethrough for the guidewire to pass. Inside the housing can be positioned an internal spring, piston, or other actuator that can push the guidewire forcefully through the stent wall to create a fenestration. The actuator can be coupled to a trigger that can be used to manually compress the spring/piston, where it can be held/locked in a loaded position temporarily, and then the trigger can be release to release the compressed spring/piston to forcefully advance the guidewire. The device of FIGS. 19-20 can be coupled to a proximal portion of the guidewire outside of the patient, while the guidewire runs through the vasculature and into the stent graft. Once the desired location of a fenestration is located using any of the devices disclosed herein, the puncturing device can be positioned over a guidewire and then can be used to advance the guidewire through the target location in the stent wall. Doing so can move the distal end of the guidewire through the sensing/locating device in certain embodiments, such that the sensing/locating device guide the advancing guidewire through the desired portion of the stent wall. Such a mechanical puncturing device can be used as an alternative to a laser-based fenestration creation system, as in described herein in some embodiments.

Characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims and their equivalents.

The invention claimed is:

1. A system comprising:
a light emitter configured to be positioned in a branch vessel and configured to emit light from within the branch vessel; and
an endovascular device comprising a light detector configured to be positioned in a main vessel, wherein the branch vessel branches off from the main vessel, wherein the endovascular device further comprises a fenestration former and a guidewire director, wherein the light detector comprises an array of optical detectors arranged on a distal face of the endovascular device, and wherein a distal end portion of the fenestration former and a distal end portion of the guidewire director are positioned radially within the array of optical detectors at the distal face;
wherein the light detector is configured to detect the light emitted by the light emitter from within the branch vessel while the light detector is positioned in the main vessel, to determine an anatomical location of an orifice of the branch vessel.

2. The system of claim 1, wherein the array of optical detectors comprises an annular array of fiber optics.

3. The system of claim 1, wherein the light emitter is coupled to a first endovascular shaft configured to extend through the main vessel and into the branch vessel, and wherein the endovascular device further comprises a second endovascular shaft configured to extend into the main vessel, and wherein the first shaft and the second shaft are independently insertable into the main vessel.

4. The system of claim 1, wherein the fenestration former comprises a laser configured for forming a fenestration in an implanted stent graft at the determined location of the orifice of the branch vessel.

5. The system of claim 4, wherein the guidewire director is a tubular guide configured to direct a guidewire through the fenestration formed in the stent graft.

6. The system of claim 1, wherein the array of optical detectors comprises an array of phototransistors coupled to a printed circuit board.

7. An endovascular device comprising:
an optical receiver that determines a location of an orifice of a branch vessel by receiving light from at least one of a light emitter positioned in the branch vessel or a light emitter positioned in a main vessel while the endovascular device is inside of a stent graft that is implanted in the main vessel and overlaps the orifice of the branch vessel;
a fenestration former that forms a fenestration in a wall of the stent graft at the determined location of the orifice of the branch vessel; and
a guidewire director that directs a guidewire through the fenestration;
wherein the optical receiver comprises an array of optical detectors arranged on a distal face of the endovascular device, and wherein a distal end portion of the fenestration former and a distal end portion of the guidewire director are positioned radially within the array of the optical detectors at the distal face.

8. The device of claim 7, wherein the array of optical detectors comprises an annular array of fiber optics.

9. The device of claim 7, wherein the array of optical detectors comprises an array of phototransistors.

10. The device of claim 7, wherein the fenestration former comprises a laser component configured to direct a laser beam at the wall of the stent graft at the determined location of the orifice of the branch vessel.

11. The device of claim 7, wherein the guidewire director comprises a tubular guide that is oriented to direct a guidewire through the fenestration.

12. The device of claim 8, wherein a distal end portion of the device comprises an inner wall positioned radially within the annular array of fiber optics, wherein the fenestration former and the guidewire director are positioned radially within the inner wall.

13. The device of claim 9, wherein the array of phototransistors is coupled to a printed circuit board, and wherein the array of phototransistors is configured to output an electrical signal in response to receiving light.

14. The device of claim 7, wherein a distal end of the endovascular device flexes at least 90 degrees to point the distal face toward the wall of the implanted stent graft.

15. The device of claim 7, wherein the fenestration former comprises a mechanical puncture device configured to puncture the wall of the stent graft at the determined location of the orifice of the branch vessel.

16. The device of claim 15, wherein the mechanical puncture device comprises an outer housing having an actuator mechanism disposed therein and a channel forming the guidewire director for receiving the guidewire therethrough.

17. The device of claim 7, wherein the distal face of the endovascular device comprises a distal end housing for supporting the array of the optical detectors.

18. The device of claim 8, wherein fiber optics within the annular array of fiber optics are on an outside of the device and are bound together.

19. The device of claim 13, wherein the distal face further comprises a printed circuit board having the phototransistors coupled thereto, and wherein the printed circuit board is foldable or collapsible for passage through vasculature.

20. The device of claim 7, wherein a distal end portion of the device comprises an inner wall positioned radially within the annular array of optical detectors, wherein the fenestration former and the guidewire director are positioned radially within the inner wall.

21. A method of utilizing the endovascular device of claim 7, the method comprising:

positioning the endovascular device in the main vessel, wherein the branch vessel branches off from the main vessel;

detecting light from the light emitter with the array of optical detectors arranged on the distal face of the endovascular device; and determining the location of the branch vessel based on the detected light.

22. The method of claim 21, further comprising:

positioning the stent graft in the main vessel overlapping the orifice of the branch vessel, wherein the endovascular device and the light emitter are positioned inside the stent graft; and forming, with the fenestration former, the fenestration in the wall of the stent graft at the determined location of the branch vessel.

23. The method of claim 21, further comprising:

positioning the stent graft in the main vessel overlapping the orifice of the branch vessel, wherein the endovascular device is positioned inside the stent graft and the light emitter is positioned in the branch vessel; and forming, with the fenestration former, the fenestration in the wall of the stent graft at the determined location of the branch vessel.

24. An endovascular device comprising:

an optical receiver that determines a location of an orifice of a branch vessel by receiving light from a light emitter while the endovascular device is inside of a stent graft that is implanted in a main vessel and overlaps the orifice of the branch vessel;

a fenestration former component comprising at least one of a laser or a mechanical puncture device for forming a fenestration in a wall of the stent graft at the determined location of the orifice of the branch vessel; and a tubular guide component oriented for directing a guidewire through the fenestration;

wherein the optical receiver comprises an array of optical detectors arranged on a distal face of the endovascular device, and wherein a distal end portion of the fenestration former component and a distal end portion of the tubular guide component are positioned radially within the array of the optical detectors at the distal face; and wherein a distal end portion of the endovascular device curves at least 90 degrees to orient the distal face toward the wall of the implanted stent graft.

* * * * *